(12) United States Patent
Laible et al.

(10) Patent No.: US 8,455,231 B2
(45) Date of Patent: Jun. 4, 2013

(54) CELL-FREE SYSTEM FOR SYNTHESIZING MEMBRANE PROTEINS CELL FREE METHOD FOR SYNTHESIZING MEMBRANE PROTEINS

(75) Inventors: Philip D. Laible, Villa Park, IL (US); Deborah K. Hanson, Villa Park, IL (US)

(73) Assignee: Uchicago Argonne, LLC, Chicago, IL (US)

( * ) Notice: Subject to any disclaimer, the term of this patent is extended or adjusted under 35 U.S.C. 154(b) by 518 days.

(21) Appl. No.: 12/702,167

(22) Filed: Feb. 8, 2010

(65) Prior Publication Data

US 2011/0244524 A1 Oct. 6, 2011

Related U.S. Application Data

(60) Provisional application No. 61/150,436, filed on Feb. 6, 2009.

(51) Int. Cl.
*C12N 9/10* (2006.01)
(52) U.S. Cl.
USPC ............... 435/193; 435/173.7; 435/307.1
(58) Field of Classification Search
None
See application file for complete search history.

(56) References Cited

U.S. PATENT DOCUMENTS 6,465,216 B2  10/2002  Laible et al.

OTHER PUBLICATIONS

I. Arechaga, B. Miroux, S. Karrasch, R. Huijbregts, B. De Kruijff, M.J. Runswick, J.E. Walker (2002) Characterization of new intracellular membranes in *Escherichia coli* accompanying large scale over-production of the b subunit of F(1) F(o) ATP Synthase. FEBS Letters 482, pp. 215-219.
B. Miroux and J.E. Walker (1996) "Over-production of proteins in *Escherichia coli*: Mutant hosts that allow synthesis of some membrane proteins and globular proteins at high levels" Journal of Molecular Biology 260, pp. 289-298.
Korepanova, et al., Biochemical Society Transactions 27, pp. 908-912 (1999), Protein Scient 14:148-158 (2005).
Columbus et al, Protein Science (2006) 15 pp. 961-975.
D. Troschel, S. Eckhardt, HK Hoffschulte, and M. Muller, Cell-free synthesis and membrane integration of the reaction center subunit H from *Rhodobacter capsulatus*. (1992) FEMS Microbiol Lett 91: pp. 129-133.
Scott, et al. "Sequences of versatile broad-host-range vectors of the RK2 family" Plasmid 50 (2003), pp. 74-79.
H. Myllykallio, et al., "Cytochrome cy of *Rhodobacter capsulatus* is attached to the cytoplasmic membrane by an uncleaved signal sequence-like anchor" J. Bacteriol (1997) 179(8) pp. 2623-2631.
Nakamura, et al., Nucl Acids Res. 28, (2000), 292.

P.H. Laible, H.N. Scott, L. Henry, D.K. Hanson "Towards higher-throughput membrane protein production for structure genomics initiatives," Journal of Structural and Functional Genomics 5 (2004), pp. 167-172.
J. Takemoto, R.C. Bachmann "Orientation of chromatophores and spheroplast-derived membrane vesicles of *Rhodopseudomonas sphaeroides*: analysis by localization of enzyme activities." (1979) Arch Biochem Biophys 195, pp. 526-534.
C. Jungas, J. L. Ranck, J. L. Rigaud, P. Joliot, A. Vermeglio (1999) Supramolecular organization of the photosynthetic apparatus of *Rhodobacter sphaeroides*, Embol J. 18, pp. 534-542.
C.A. Siebert, P. Qian, D. Fotiadis, A. Engel, C.N. Hunter, P.A. Bullough "Molecular architecture of photosynthetic membranes in *Rhodobacter sphaeroides*" the Role of PufX, (2004) Embo J 23, pp. 690-700.
R. Dierstein, A. Schumacher, G. Drews, on the insertion of pigment-associated polypeptides during membrane biogenesis in *Rhodopseudomonas capsulata*. (1981) Archives of Microbiology 128, pp. 376-383.
M.A. Lommen and J. Takemoto, Comparison, by freeze-fracture electronic microscopy , of chromatophores, spheroplast-derived membrane vesicles, and whole cells of *Rhodopseudo-monas sphaeroides*, (1978) J Bacteriol 136, pp. 730-741.
P.A. Reilly and R.A. Niederman, Role of apparent membrane growth initiation sites during photosynthetic membrane development in synchronously dividing *Rhodoseudomonas sphaeroides* (1986) J Bacteriol 167, pp. 153-159.
C.J. Marx and M.E. Lidstrom, Broad-host-range cre-lox system for antibiotic recycling in gram-negative bacteria (2002), Biotechniques 33, pp. 1062-1067.
J. Chory and S. Kaplan, The in vitro transcription-translation of DNA and RNA templates by extracts of *Rhodoseudomonas sphaeroides*. Optimization and comparison of templates specificity with *Escherichia coli* extracts and in vivo synthesis (1982) J Biol Chem 257, pp. 15110-15121.
D. Troschel and M. Muller, Development of a cell-free system to study the membrane assembly of photosynthetic proteins of *Rhodobacter capsulatus* (1990) J Cell Bio 111, pp. 87-94.
H. Keifer, et. al, "Refolding of G-protein-coupled receptors from inclusion bodies produced in *Escherichia cells*", Biochemical Society Transactions 27, pp. 908-912 (1999).

*Primary Examiner* — Jim Ketter
(74) *Attorney, Agent, or Firm* — Cherskov Flaynik & Gurda LLC

(57) ABSTRACT

The invention provides an in vitro method for producing proteins, membrane proteins, membrane-associated proteins, and soluble proteins that interact with membrane-associated proteins for assembly into an oligomeric complex or that require association with a membrane for proper folding. The method comprises, supplying intracytoplasmic membranes from organisms; modifying protein composition of intracytoplasmic membranes from organism by modifying DNA to delete genes encoding functions of the organism not associated with the formation of the intracytoplasmic membranes; generating appropriate DNA or RNA templates that encode the target protein; and mixing the intracytoplasmic membranes with the template and a transcription/translation-competent cellular extract to cause simultaneous production of the membrane proteins and encapsulation of the membrane proteins within the intracytoplasmic membranes.

20 Claims, 15 Drawing Sheets

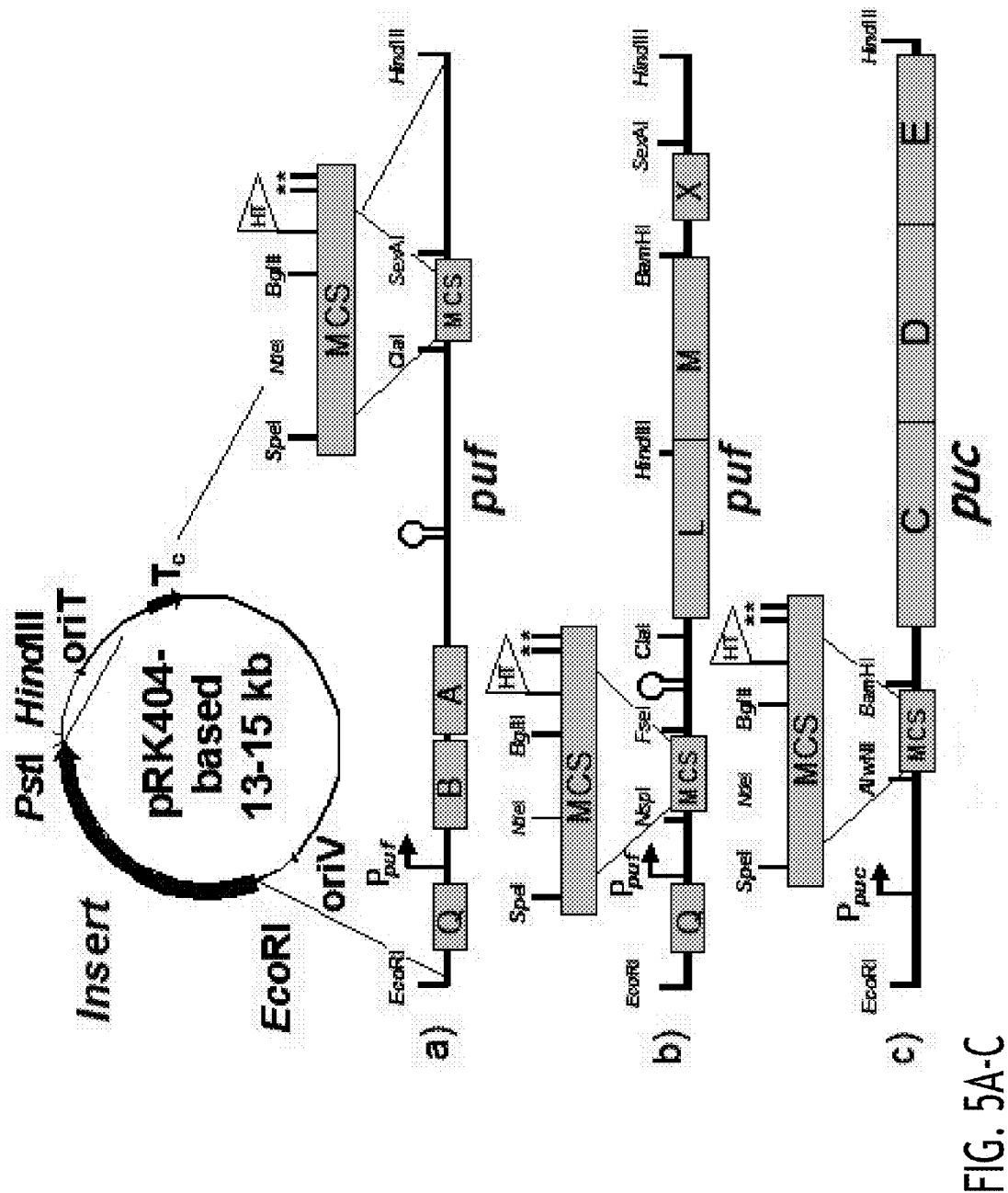
FIG. 5A-C

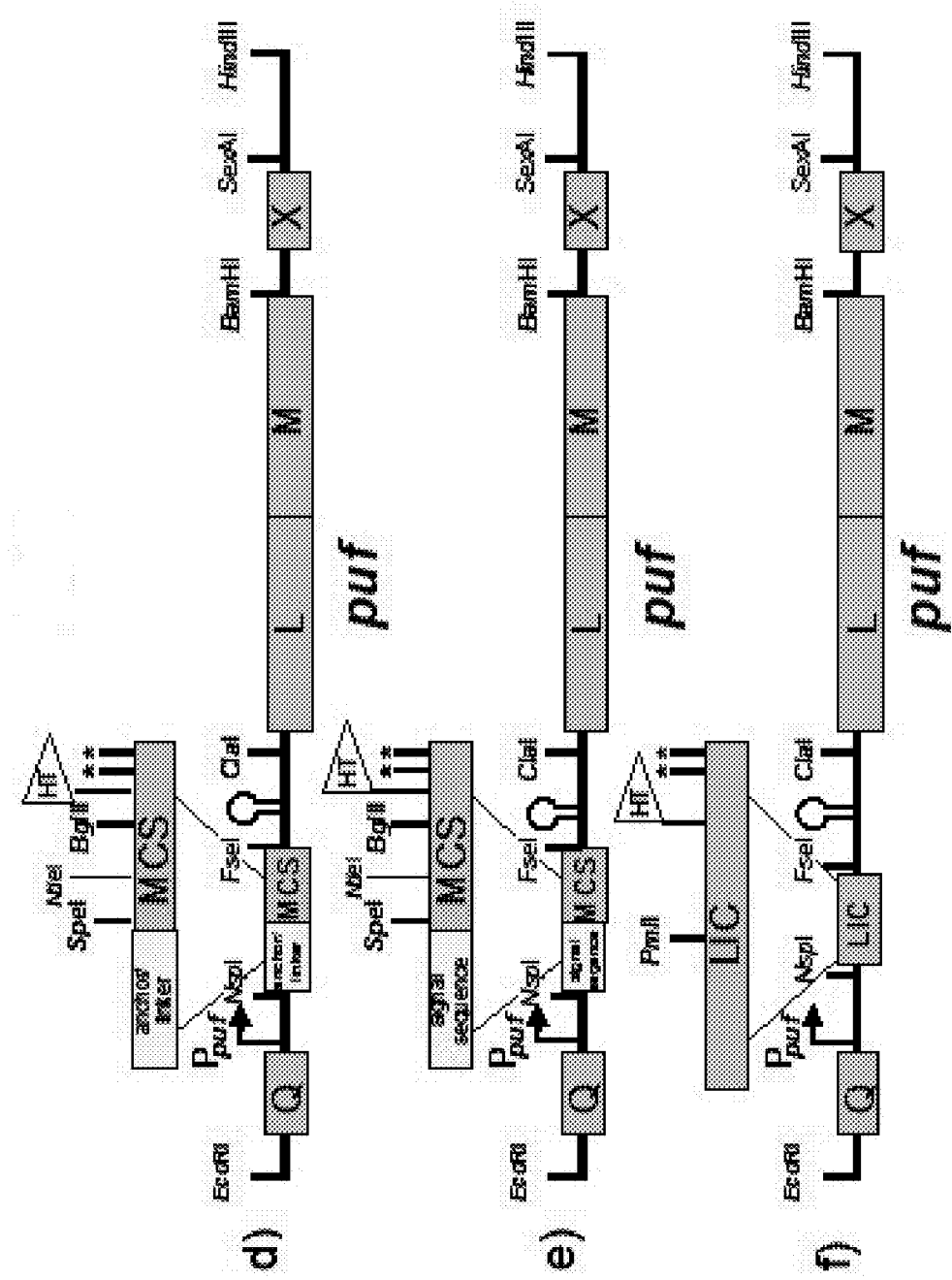
FIG. 5D-F

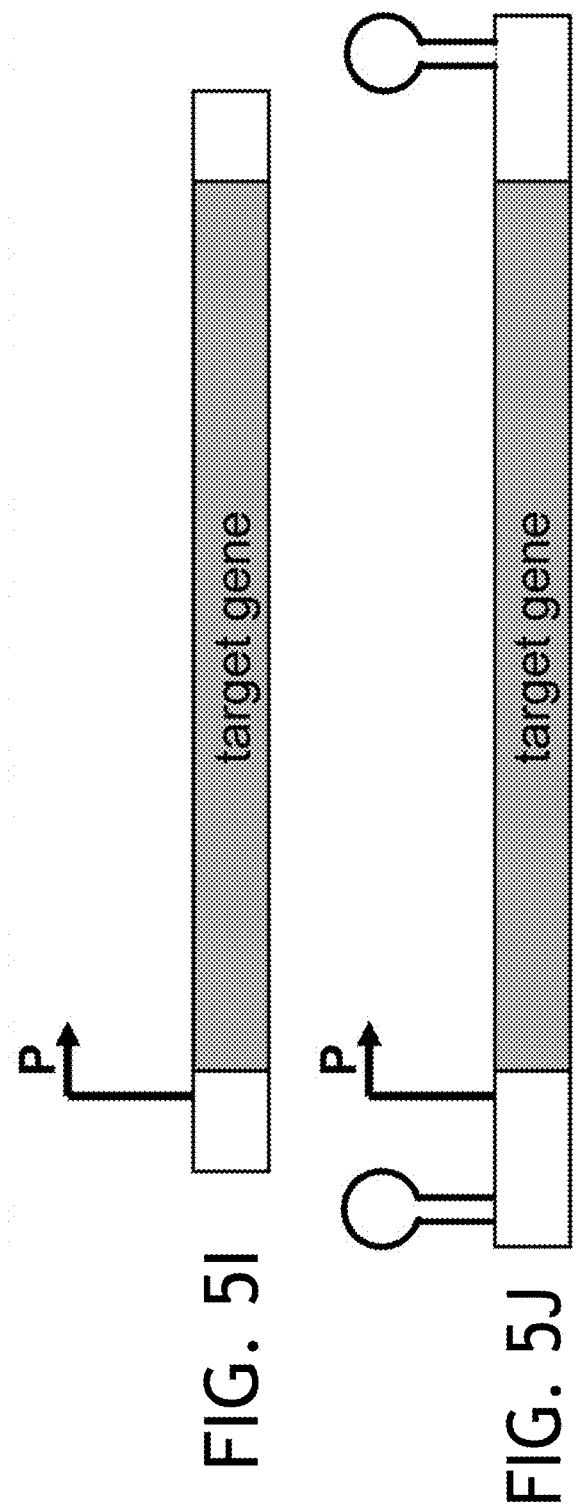

SEQUENCE LISTING

<160> NUMBER OF SEQ ID NOS: 2

<210> SEQ ID NO 1
<211> LENGTH: 11237
<212> TYPE: DNA
<213> ORGANISM: Artificial Sequence
<220> FEATURE:
<223> OTHER INFORMATION: Cloning vector pRK404

<400> SEQUENCE: 1

```
gaattcaccc ccgaacacga gcacggcacc cgcgaccact atgccaagaa tgcccaaggt      60
aaaaattgcc ggccccgcca tgaagtccgt gaatgccccg acggccgaag tgaagggcag     120
gccgccaccc aggccgccgc cctcactgcc cggcacctgg tcgctgaatg tcgatgccag     180
cacctgcggc acgtcaatgc ttccgggcgt cgcgctcggg ctgatcgccc atcccgttac     240
tgccccgatc ccggcaatgg caaggactgc cagcgctgcc atttttgggg tgaggccgtt     300
cgcggccgag gggcgcagcc cctgggggga tgggaggccc gcgttagcgg gccgggaggg     360
ttcgagaagg gggggcaccc cccttcggcg tgcgcggtca cgcgcacagg gcgcagccct     420
ggttaaaaac aaggtttata aatattggtt taaaagcagg ttaaaagaca ggttagcggt     480
ggccgaaaaa cgggcggaaa cccttgcaaa tgctggattt tctgcctgtg gacagcccct     540
caaatgtcaa taggtgcgcc cctcatctgt cagcactctg cccctcaagt gtcaaggatc     600
gcgcccctca tctgtcagta gtcgcgcccc tcaagtgtca ataccgcagg gcacttatcc     660
ccaggcttgt ccacatcatc tgtgggaaac tcgcgtaaaa tcaggcgttt tcgccgattt     720
gcgaggctgg ccagctccac gtcgccggcc gaaatcgagc ctgcccctca tctgtcaacg     780
ccgcgccggg tgagtcggcc cctcaagtgt caacgtccgc ccctcatctg tcagtgaggg     840
ccaagttttc cgcgaggtat ccacaacgcc ggcggccgcg gtgtctcgca cacggcttcg     900
acggcgtttc tggcgcgttt gcagggccat agacggccgc cagcccagcg cgagggcaa     960
ccagcccggt gagcgtcgga aggcgctct tccgcttcct cgctcactga ctcgctgcgc    1020
tcggtcgttc ggctgcggcg agcggtatca gctcactcaa aggcggtaat acggttatcc    1080
acagaatcag gggataacgc aggaaagaac atgtgagcaa aaggccagca aaaggccagg    1140
```

```
aaccgtaaaa aggccgcgtt gctggcgttt ttccataggc tccgcccccc tgacgagcat    1200
cacaaaaatc gacgctcaag tcagaggtgg cgaaacccga caggactata aagataccag    1260
gcgtttcccc ctggaagctc cctcgtgcgc tctcctgttc cgaccctgcc gcttaccgga    1320
tacctgtccg cctttctccc ttcgggaagc gtggcgccat tcgccattca ggctgcgcaa    1380
ctgttgggaa gggcgatcgg tgcgggcctc ttcgctatta cgccagctgg cgaaaggggg    1440
atgtgctgca aggcgattaa gttgggtaac gccaggg ttt tcccagtcac gacgttgtaa    1500
aacgacggcc agtgaattcc cggggatccg tcgacctgca gccaagcttg cgtaatcat     1560 ggtcatagct gtttcctgtg tgaaattgtt atccgctcac aattccacac aacatacgag    1620
ccggaagcat aaagtgtaaa gcctggggtg cctaatgagt gagctaactc acattaattg    1680
cgttgcgctc actgcccgct ttccagtcgg gaaacctgtc gtgccagctg cattaatgaa    1740
tcggccaacg cgcggggaga ggcggtttgc gtattgggcg ctcggtcttg ccttgctcgt    1800
cggtgatgta cttcaccagc tccgcgaagt cgctcttctt gatggagcgc atggggacgt    1860
gcttggcaat cacgcgcacc ccccggccgt tttagcggct aaaaaagtca tggctctgcc    1920
ctcgggcgga ccacgcccat catgaccttg ccaagctcgt cctgcttctc ttcgatcttc    1980
gccagcaggg cgaggatcgt ggcatcaccg aaccgcgccg tgcgcgggtc gtcggtgagc    2040
cagagtttca gcaggccgcc caggcggccc aggtcgccat tgatgcgggc cagctcgcgg    2100
acgtgctcat agtccacgac gcccgtgatt ttgtagccct ggccgacggc cagcaggtag    2160
gccgacaggc tcatgccggc cgccgccgcc ttttcctcaa tcgctcttcg ttcgtctgga    2220
aggcagtaca ccttgatagg tgggctgccc ttcctggttg gcttggtttc atcagccatc    2280
cgcttgccct catctgttac gccggcggta gccggccagc ctcgcagagc aggattcccg    2340
ttgagcaccg ccaggtgcga ataagggaca gtgaagaagg aacacccgct cgcgggtggg    2400
cctacttcac ctatcctgcc cggctgacgc cgttggatac accaaggaaa gtctacacga    2460 acccttggc aaaatcctgt atatcgtgcg aaaaaggatg gatataccga aaaatcgct     2520 ataatgaccc cgaagcaggg ttatgcagcg gaaaagcgcc acgcttcccg aagggagaaa    2580
ggcggacagg tatccggtaa gcggcagggt cggaacagga gagcgcacga gggagcttcc    2640
agggggaaac gcctggtatc tttatagtcc tgtcgggttt cgccacctct gacttgagcg    2700
tcgatttttg tgatgctcgt caggggggcg gagcctatgg aaaaacgcca gcaacgcggc    2760 cttttttacgg ttcctggcct tttgctggcc ttttgctcac atgttctttc ctgcgttatc    2820
ccctgattct gtggataacc gtattaccgc ctttgagtga gctgataccg ctcgccgcag    2880
ccgaacgacc gagcgcagcg agtcagtgag cgaggaagcg gaagagcgcc agaaggccgc    2940
cagagaggcc gagcgcggcc gtgaggcttg acgctaggg cagggcatga aaaagcccgt     3000
agcgggctgc tacgggcgtc tgacgcggtg gaaaggggga ggggatgttg tctacatggc    3060
tctgctgtag tgagtgggtt gcgctccggc agcggtcctg atcaatcgtc acccttttctc   3120 ggtccttcaa cgttcctgac aacgagcctc cttttcgcca atccatcgac aatcaccgcg    3180
agtccctgct cgaacgctgc gtccggaccg gcttcgtcga aggcgtctat cgcggcccgc    3240
aacagcggcg agagcggagc ctgttcaacg gtgccgccgc gctcgccggc atcgctgtcg    3300
ccggcctgct cctcaagcac ggccccaaca gtgaagtagc tgattgtcat cagcgcattg    3360
acggcgtccc cggccgaaaa acccgcctcg cagaggaagc gaagctgcgc gtcggccgtt    3420
tccatctgcg gtgcgcccgg tcgcgtgccg gcatggatgc gcgcgccatc gcggtaggcg    3480
agcagcgcct gcctgaagct gcgggcattc ccgatcagaa atgagcgcca gtcgtcgtcg    3540
```

```
gctctcggca ccgaatgcgt atgattctcc gccagcatgg cttcggccag tgcgtcgagc   3600
agcgcccgct tgttcctgaa gtgccagtaa agcgccggct gctgaacccc caaccgttcc   3660
gccagtttgc gtgtcgtcag accgtctacg ccgacctcgt tcaacaggtc cagggcggca   3720
cggatcactg tattcggctg caactttgtc atgcttgaca ctttatcact gataaacata   3780
atatgtccac caacttatca gtgataaaga atccgcgcgt tcaatcggac cagcggaggc   3840
tggtccggag gccagacatg aaacccaaca taccctgat cgtaattctg agcactgtcg   3900
cgctcgacgc tgtcggcatc ggcctgatta tgccggtgct gccgggcctc ctgcgcgatc   3960
tggttcactc gaacgacgtc accgcccact atggcattct gctggcgctg tatgcgttgg   4020
tgcaatttgc ctgcgcacct gtgctgggcg cgctgtcgga tcgtttcggg cggcggccaa   4080
tcttgctcgt ctcgctggcc ggcgccactg tcgactacgc catcatggcg acagcgcctt   4140
tcctttgggt tctctatatc gggcggatcg tggccggcat caccggggcg actggggcgg   4200
tagccggcgc ttatattgcc gatatcactg atggcgatga gcgcgcgcgg cacttcggct   4260
tcatgagcgc ctgtttcggg ttcggatgg tcgcgggacc tgtgctcggt gggctgatgg   4320
gcggtttctc ccccacgct ccgttcttcg ccgcggcagc cttgaacggc ctcaatttcc   4380
tgacgggctg tttcctttg ccggagtcgc acaaaggcga acgccggccg ttacgccggg   4440
aggctctcaa cccgctcgct tcgttccggt gggcccgggg catgaccgtc gtcgccgccc   4500
tgatggcggt cttcttcatc atgcaacttg tcggacaggt gccggccgcg ctttgggtca   4560
ttttcggcga ggatcgcttt cactgggacg cgaccacgat cggcatttcg cttgccgcat   4620
ttggcattct gcattcactc gcccaggcaa tgatcaccgg ccctgtagcc gcccggctcg   4680
gcgaaaggcg ggcactcatg ctcggaatga ttgccgacgg cacaggctac atcctgcttg   4740
ccttcgcgac acggggatgg atggcgttcc cgatcatggt cctgcttgct cgggtggca   4800 tcggaatgcc ggcgctgcaa gcaatgttgt ccaggcaggt ggatgaggaa cgtcaggggc   4860
agctgcaagg ctcactggcg gcgctcacca gcctgacctc gatcgtcgga cccctcctct   4920
tcacggcgat ctatgcggct tctataacaa cgtggaacgg gtgggcatgg attgcaggcg   4980
ctgccctcta cttgctctgc ctgccggcgc tgcgtcgcgg gctttggagc ggcgcagggc   5040
aacgagccga tcgctgatcg tggaaacgat aggcctatgc catgcgggtc aaggcgactt   5100
ccggcaagct atacgcgccc taggagtgcg gttggaacgt tggcccagcc agatactccc   5160
gatcacgagc aggacgccga tgatttgaag cgcactcagc gtctgatcca agaacaacca   5220
tcctagcaac acgcggtcc ccgggctgag aaagcccagt aaggaaacaa ctgtaggttc   5280
gagtcgcgag atcccccgga accaaaggaa gtaggttaaa cccgctccga tcaggccgag   5340
ccacgccagg ccgagaacat tggttcctgt aggcatcggg attggcggat caaacactaa   5400
agctactgga acgagcagaa gtcctccggc cgccagttgc caggcggtaa aggtgagcag   5460
aggcacggga ggttgccact tgcgggtcag cacggttccg aacgccatgg aaaccgcccc   5520
cgccaggccc gctgcgacgc cgacaggatc tagcgctgcg tttggtgtca acaccaacag   5580
cgccacgccc gcagttccgc aaatagcccc caggaccgcc atcaatcgta tcgggctacc   5640
tagcagagcg gcagagatga acacgaccat cagcggctgc acagcgccta ccgtcgccgc   5700
gaccccgccc ggcaggcggt agaccgaaat aaacaacaag ctccagaata gcgaaatatt   5760
aagtgcgccg aggatgaaga tgcgcatcca ccagattccc gttggaatct gtcggacgat   5820
catcacgagc aataaacccg ccggcaacgc ccgcagcagc ataccggcga ccctcggcc   5880 tcgctgttcg ggctccacga aaacgccgga cagatgcgcc ttgtgagcgt ccttggggcc   5940
```

```
gtcctcctgt ttgaagaccg acagcccaat gatctcgccg tcgatgtagg cgccgaatgc    6000
cacggcatct cgcaaccgtt cagcgaacgc ctccatgggc tttttctcct cgtgctcgta    6060
aacggacccg aacatctctg gagctttctt cagggccgac aatcggatct cgcggaaatc    6120
ctgcacgtcg gccgctccaa gccgtcgaat ctgagcctta atcacaattg tcaattttaa    6180
tcctctgttt atcggcagtt cgtagagcgc gccgtgcgtc ccgagcgata ctgagcgaag    6240
caagtgcgtc gagcagtgcc cgcttgttcc tgaaatgcca gtaaagcgct ggctgctgaa    6300
cccccagccg gaactgaccc cacaaggccc tagcgtttgc aatgcaccag gtcatcattg    6360
acccaggcgt gttccaccag gccgctgcct cgcaactctt cgcaggcttc gccgacctgc    6420
tcgcgccact tcttcacgcg ggtggaatcc gatccgcaca tgaggcggaa ggtttccagc    6480
ttgagcgggt acggctcccg gtgcgagctg aaatagtcga acatccgtcg ggccgtcggc    6540
gacagcttgc ggtacttctc ccatatgaat ttcgtgtagt ggtcgccagc aaacagcacg    6600
acgatttcct cgtcgatcag gacctggcaa cgggacgttt tcttgccacg gtccaggacg    6660
cggaagcggt gcagcagcga caccgattcc aggtgcccaa cgcggtcgga cgtgaagccc    6720
atcgccgtcg cctgtaggcg cgacaggcat tcctcggcct tcgtgtaata ccggccattg    6780
atcgaccagc ccaggtcctg gcaaagctcg tagaacgtga aggtgatcgg ctcgccgata    6840
ggggtgcgct tcgcgtactc caacacctgc tgccacacca gttcgtcatc gtcggcccgc    6900
agctcgacgc cggtgtaggt gatcttcacg tccttgttga cgtggaaaat gaccttgttt    6960
tgcagcgcct cgcgcgggat tttcttgttg cgcgtggtga acagggcaga gcgggccgtg    7020
tcgtttggca tcgctcgcat cgtgtccggc cacgcgcaa tatcgaacaa ggaaagctgc    7080
atttccttga tctgctgctt cgtgtgtttc agcaacgcgg cctgcttggc ctcgctgacc    7140
tgttttgcca ggtcctcgcc ggcggttttt cgcttcttgg tcgtcatagt tcctcgcgtg    7200
tcgatggtca tcgacttcgc caaacctgcc gcctcctgtt cgagacgacg cgaacgctcc    7260
acggcggccg atggcgcggg cagggcaggg ggagccagtt gcacgctgtc gcgctcgatc    7320
ttggccgtag cttgctggac catcgagccg acggactgga aggtttcgcg gggcgcacgc    7380
atgacggtgc ggcttgcgat ggtttcggca tcctcggcgg aaaaccccgc gtcgatcagt    7440
tcttgcctgt atgccttccg gtcaaacgtc cgattcattc ccctccttg cgggattgcc    7500 ccgactcacg ccggggcaat gtgcccttat tcctgatttg acccgcctgg tgccttggtg    7560
tccagataat ccaccttatc ggcaatgaag tcggtcccgt agaccgtctg gccgtccttc    7620
tcgtacttgg tattccgaat cttgccctgc acgaatacca gcgaccccct gcccaaatac    7680
ttgccgtggg cctcggcctg agagccaaaa cacttgatgc ggaagaagtc ggtgcgctcc    7740
tgcttgtcgc cggcatcgtt gcgccactct tcattaaccg ctatatcgaa aattgcttgc    7800
ggcttgttag aattgccatg acgtacctcg gtgtcacggg taagattacc gataaactgg    7860
aactgattat ggctcatatc gaaagtctcc ttgagaaagg agactctagt ttagctaaac    7920
attggttccg ctgtcaagaa ctttagcggc taaaattttg cgggccgcga ccaaaggtgc    7980 gagggcggc ttccgctgtg tacaaccaga tattttcac caacatcctt cgtctgctcg    8040
atgagcgggg catgacgaaa catgagctgt cggagagggc aggggtttca atttcgtttt    8100
tatcagactt aaccaacggt aaggccaacc cctcgttgaa ggtgatggag ccattgccg    8160 acgccctgga aactccccta cctcttctcc tggagtccac cgaccttgac cgcgaggcac    8220
tcgcggagat tgcgggtcat cctttcaaga gcagcgtgcc gccgggatac gaacgcatca    8280
gtgtggtttt gccgtcacat aaggcgttta tcgtaaagaa atggggcgac gacacccgaa    8340
```

```
aaaagctgcg tggaaggctc tgacgccaag ggttagggct tgcacttcct tctttagccg   8400
ctaaaacggc cccttctctg cgggccgtcg gctcgcgcat catatcgaca tcctcaacgg   8460
aagccgtgcc gcgaatggca tcgggcgggt gcgctttgac agttgttttc tatcagaacc   8520
cctacgtcgt gcggttcgat tagctgtttg tcttgcaggc taaacacttt cggtatatcg   8580
tttgcctgtg cgataatgtt gctaatgatt tgttgcgtag gggttactga aaagtgagcg   8640
ggaaagaaga gtttcagacc atcaaggagc gggccaagcg caagctggaa cgcgacatgg   8700
gtgcggacct gttggccgcg ctcaacgacc cgaaaaccgt tgaagtcatg ctcaacgcgg   8760
acggcaaggt gtggcacgaa cgccttggcg agccgatgcg gtacatctgc gacatgcggc   8820
ccagccagtc gcaggcgatt atagaaacgg tggccggatt ccacggcaaa gaggtcacgc   8880
ggcattcgcc catcctggaa ggcgagttcc ccttggatgg cagccgcttt gccggccaat   8940
tgccgccggt cgtggccgcg ccaacctttg cgatccgcaa gcgcgcggtc gccatcttca   9000
cgctggaaca gtacgtcgag gcgggcatca tgacccgcga gcaatacgag gtcattaaaa   9060
gcgccgtgat tgatgatata gcggcccggc tgctcctggt tctcgcgcac cgaaatgggt   9120
gacttcaccc cgcgctcttt gatcgtggca ccgatttccg cgatgctctc cggggaaaag   9180
ccggggttgt cggccgtccg cggctgatgc ggatcttcgt cgatcaggtc caggtccagc   9240
tcgatagggc cggaaccgcc ctgagacgcc gcaggagcgt ccaggaggct cgacaggtcg   9300
ccgatgctat ccaaccccag gccggacggc tgcgccgcgc ctgcggcttc ctgagcggcc   9360
gcagcggtgt ttttcttggt ggtcttggct tgagccgcag tcattgggaa atctccatct   9420
tcgtgaacac gtaatcagcc agggcgcgaa cctctttcga tgccttgcgc gcggccgttt   9480
tcttgatctt ccagaccggc acaccggatg cgagggcatc ggcgatgctg ctgcgcaggc   9540
caacggtggc cggaatcatc atcttggggt acgcggccag cagctcggct tggtggcgcg   9600
cgtggcgcgg attccgcgca tcgaccttgc tgggcaccat gccaaggaat tgcagcttgg   9660
cgttcttctg gcgcacgttc gcaatggtcg tgaccatctt cttgatgccc tggatgctgt   9720
acgcctcaag ctcgatgggg gacagcacat agtcggccgc gaagagggcg gccgccaggc   9780
cgacgccaag ggtcggggcc gtgtcgatca ggcacacgtc gaagccttgg ttcgccaggg   9840
ccttgatgtt cgccccgaac agctcgcggg cgtcgtccag cgacagccgt tcggcgttcg   9900
ccagtaccgg gttggactcg atgagggcga ggcgcgcggc ctggccgtcg ccggctgcgg   9960
gtgcggtttc ggtccagccg ccggcaggga cagcgccgaa cagcttgctt gcatgcaggc   10020
cggtagcaaa gtccttgagc gtgtaggacg cattgccctg ggggtccagg tcgatcacgg   10080
caacccgcaa gccgcgctcg aaaaagtcga aggcaagatg cacaagggtc gaagtcttgc   10140
cgacgccgcc tttctggttg gccgtgacca agtttttcat cgtttggttt cctgtttttt   10200
cttggcgtcc gcttcccact tccggacgat gtacgcctga tgttccggca gaaccgccgt   10260
tacccgcgcg taccccctcgg gcaagttctt gtcctcgaac gcggcccaca cgcgatgcac   10320
cgcttgcgac actgcgcccc tggtcagtcc cagcgacgtt gcgaacgtcg cctgtggctt   10380
cccatcgact aagacgcccc gcgctatctc gatggtctgc tgccccactt ccagcccctg   10440
gatcgcctcc tggaactggc tttcggtaag ccgtttcttc atggataaca cccataattt   10500
gctccgcgcc ttggttgaac atagcggtga cagccgccag cacatgagag aagtttagct   10560
aaacatttct cgcacgtcaa caccttttagc cgctaaaact cgtccttggc gtaacaaaac   10620
aaaagcccgg aaacccgggct ttcgtctctt gccgcttatg gctctgcacc cggctccatc   10680
accaacaggt cgcgcacgcg cttcactcgg ttgcggatcg acactgccag cccaacaaag   10740
```

```
ccggttgccg  ccgccgccag  gatcgcgccg  atgatgccgg  ccacaccggc  catcgcccac    10800
caggtcgccg  ccttccggtt  ccattcctgc  tggtactgct  tcgcaatgct  ggacctcggc    10860
tcaccatagg  ctgaccgctc  gatggcgtat  gccgcttctc  cccttggcgt  aaaacccagc    10920
gccgcaggcg  gcattgccat  gctgcccgcc  gctttcccga  ccacgacgcg  cgcaccaggc    10980
ttgcggtcca  gaccttcggc  cacggcgagc  tgcgcaagga  cataatcagc  cgccgacttg    11040
gctccacgcg  cctcgatcag  ctcttgcact  cgcgcgaaat  ccttggcctc  cacggccgcc    11100
atgaatcgcg  cacgcggcga  aggctccgca  gggccggcgt  cgtgatcgcc  gccgagaatg    11160
cccttcacca  agttcgacga  cacgaaaatc  atgctgacgg  ctatcaccat  catgcagacg    11220
gatcgcacga  acccgct                                                       11237

<210> SEQ ID NO 2
<211> LENGTH: 9820
<212> TYPE: DNA
<213> ORGANISM: Artificial Sequence
<220> FEATURE:
<223> OTHER INFORMATION: Cloning vector pRK442(H)

<400> SEQUENCE: 2
ccacccaggc  cgccgccctc  actgccggca  acctggtcgc  tgaatgtcga  tgccagcacc      60
tgcggcacgt  caatgcttcc  gggcgtcgcg  ctcgggctga  tcgcccatcc  cgttactgcc     120
ccgatcccgg  caatggcaag  gactgccagc  gctgccattt  tgggggtgag  gccgttcgcg     180
gccgaggggc  gcagccctg   gggggatggg  aggcccgcgt  tagcgggccg  ggagggttcg     240 agaaggggg   gcaccccct   tcggcgtgcg  cggtcacgcg  cacagggcgc  agccctggtt     300
aaaaacaagg  tttataaata  ttggtttaaa  agcaggttaa  aagacaggtt  agcggtggcc     360
gaaaaacggg  cggaaaccct  tgcaaatgct  ggattttctg  cctgtggaca  gcccctcaaa     420
tgtcaatagg  tgcgcccctc  atctgtcagc  actctgcccc  tcaagtgtca  aggatcgcgc     480
ccctcatctg  tcagtagtcg  cgcccctcaa  gtgtcaatac  cgcagggcac  ttatccccag     540
gcttgtccac  atcatctgtg  ggaaactcgc  gtaaaatcag  gcgttttcgc  cgatttgcga     600
ggctggccac  ctccacgtcg  ccggccgaaa  tcgagcctgc  ccctcatctg  tcaacgccgc     660
gccgggtgag  tcggcccctc  aagtgtcaac  gtccgcccct  catctgtcag  tgagggccaa     720
gttttccgcg  aggtatccac  aacgccggcg  gccgcggtgt  ctcgcacacg  gcttcgacgg     780
cgtttctggc  gcgtttgcag  ggccatagac  ggccgccagc  ccagcggcga  gggcaaccag     840
cccggtgagc  gtcggaaagg  cgctcttccg  cttcctcgct  cactgactcg  ctgcgctcgg     900
tcgttcggct  gcggcgagcg  gtatcagctc  actcaaaggc  ggtaatacgg  ttatccacag     960
aatcagggga  taacgcagga  aagaacatgt  gagcaaaagg  ccagcaaaag  gccaggaacc    1020
gtaaaaaggc  cgcgttgctg  gcgtttttcc  ataggctccg  cccccctgac  gagcatcaca    1080
aaaatcgacg  ctcaagtcag  aggtggcgaa  acccgacagg  actataaaga  taccaggcgt    1140
ttccccctgg  aagctccctc  gtgcgctctc  ctgttccgac  cctgccgctt  accggatacc    1200
tgtccgcctt  tctcccttcg  ggaagcgtgg  cgccattcgc  cattcaggct  gcgcaactgt    1260
tgggaagggc  gatcggtgcg  ggcctcttcg  ctattacgcc  agctggcgaa  aggggatgt    1320 gctgcaaggc  gattaagttg  ggtaacgcca  gggttttccc  agtcacgacg  ttgtaaaacg    1380
acggccagtg  aattcccggg  gatccgtcga  cctgcagcca  agctagcttg  gcgtaatcat    1440
ggtcatagct  gtttcctgtg  tgaaattgtt  atccgctcac  aattccacac  aacatacgag    1500
ccggaagcat  aaagtgtaaa  gcctggggtg  cctaatgagt  gagctaactc  acattaattg    1560
```

```
cgttgcgctc actgcccgct ttccagtcgg gaaacctgtc gtgccagctg cattaatgaa    1620
tcggccaacg cgcggggaga ggcggttttgc gtattgggcg ctcggtcttg ccttgctcgt    1680
cggtgatgta cttcaccagc tccgcgaagt cgctcttctt gatggagcgc atgggacgt     1740 gcttggcaat cacgcgcacc ccccggccgt tttagcggct aaaaaagtca tggctctgcc    1800
ctcgggcgga ccacgcccat catgaccttg ccaagctcgt cctgcttctc ttcgatcttc    1860
gccagcaggg cgaggatcgt ggcatcaccg aaccgcgccg tgcgcgggtc gtcggtgagc    1920
cagagtttca gcaggccgcc caggcggccc aggtcgccat tgatgcgggc cagctcgcgg    1980
acgtgctcat agtccacgac gcccgtgatt ttgtagccct ggccgacggc cagcaggtag    2040
gccgacaggc tcatgccggc cgccgccgcc ttttcctcaa tcgctcttcg ttcgtctgga    2100
aggcagtaca ccttgatagg tgggctgccc ttcctggttg gcttggtttc atcagccatc    2160
cgcttgccct catctgttac gccggcggta gccggccagc ctcgcagagc aggattcccg    2220
ttgagcaccg ccaggtgcga ataagggaca gtgaagaagg aacacccgct cgcgggtggg    2280
cctacttcac ctatcctgcc cggctgacgc cgttggatac accaaggaaa gtctacacga    2340 acccttggc aaaatcctgt atatcgtgcg aaaaaggatg gatataccga aaaaatcgct    2400
ataatgaccc cgaagcaggg ttatgcagcg gaaaagcgcc acgcttcccg aagggagaaa    2460
ggcggacagg tatccggtaa gcggcagggt cggaacagga gagcgcacga gggagcttcc    2520 aggggggaaac gcctggtatc tttatagtcc tgtcgggttt cgccacctct gacttgagcg    2580 tcgattttg tgatgctcgt caggggggcg gagcctatgg aaaaacgcca gcaacgcggc    2640
ctttttacgg ttcctggcct tttgctggcc ttttgctcac atgttctttc ctgcgttatc    2700
ccctgattct gtggataacc gtattaccgc ctttgagtga gctgataccg ctcgccgcag    2760
ccgaacgacc gagcgcagcg agtcagtgag cgaggaagcg gaagagcgcc agaaggccgc    2820
cagagaggcc gagcgcggcc gtgaggcttg gacgctaggg cagggcatga aaaagcccgt    2880
agcgggctgc tacgggcgtc tgacgcgtg gaaaggggga ggggatgttg tctacatggc    2940
tctgctgtag tgagtgggtt gcgctccggc agcggtcctg atcaatcgtc acccttctc    3000 ggtccttcaa cgttcctgac aacgagcctc cttttcgcca atccatcgac aatcaccgcg    3060
agtccctgct cgaacgctgc gtccggaccg gcttcgtcga aggcgtctat cgcggcccgc    3120
aacagcggcg agagcggagc ctgttcaacg gtgccgccgc gctcgccggc atcgctgtcg    3180
ccggcctgct cctcaagcac ggccccaaca gtgaagtagc tgattgtcat cagcgcattg    3240
acggcgtccc cggccgaaaa acccgcctcg cagaggaagc gaagctgcgc gtcggccgtt    3300
tccatctgcg gtgcgcccgg tcgcgtgccg gcatggatgc gcgcgccatc gcggtaggcg    3360
agcagcgcct gcctgaagct gcgggcattc ccgatcagaa atgagcgcca gtcgtcgtcg    3420
gctctcggca ccgaatgcgt atgattctcc gccagcatgg cttcggccag tgcgtcgagc    3480
agcgcccgct tgttcctgaa gtgccagtaa agcgccggct gctgaacccc caaccgttcc    3540
gccagtttgc gtgtcgtcag accgtctacg ccgacctcgt tcaacaggtc cagggcggca    3600
cggatcactg tattcggctg caactttgtc atgcttgaca ctttatcact gataaacata    3660
atatgtccac caacttatca gtgataaaga atccgcgcgt tcaatcggac cagcggaggc    3720
tggtccggag gccagacatg aaacccaaca taccccctgat cgtaattctg agcactgtcg    3780
cgctcgacgc tgtcggcatc ggcctgatta tgccggtgct gccgggcctc ctgcgcgatc    3840
tggttcactc gaacgacgtc accgcccact atggcattct gctggcgctg tatgcgttgg    3900
tgcaatttgc ctgcgcacct gtgctgggcg cgctgtcgga tcgtttcggg cggcggccaa    3960
```

-continued

```
tcttgctcgt ctcgctggcc ggcgccactg tcgactacgc catcatggcg acagcgcctt    4020
tcctttgggt tctctatatc gggcggatcg tggccggcat caccggggcg actggggcgg    4080
tagccggcgc ttatattgcc gatatcactg atggcgatga gcgcgcgcgg cacttcggct    4140
tcatgagcgc ctgtttcggg ttcggatgg tcgcgggacc tgtgctcggt gggctgatgg    4200
gcggtttctc cccccacgct ccgttcttcg ccgcggcagc cttgaacggc ctcaatttcc    4260
tgacgggctg tttccttttg ccggagtcgc acaaaggcga acgccggccg ttacgccggg    4320
aggctctcaa cccgctcgct tcgttccggt gggcccgggg catgaccgtc gtcgccgccc    4380
tgatggcggt cttcttcatc atgcaacttg tcggacaggt gccggccgcg ctttgggtca    4440
ttttcggcga ggatcgcttt cactgggacg cgaccacgat cggcatttcg cttgccgcat    4500
ttggcattct gcattcactc gcccaggcaa tgataccgg ccctgtagcc gcccggctcg    4560
gcgaaaggcg ggcactcatg ctcggaatga ttgccgacgg cacaggctac atcctgcttg    4620
ccttcgcgac acggggatgg atggcgttcc cgatcatggt cctgcttgct cgggtggca    4680 tcggaatgcc ggcgctgcaa gcaatgttgt ccaggcaggt ggatgaggaa cgtcaggggc    4740
agctgcaagg ctcactggcg cgctcacca gcctgacctc gatcgtcgga cccctcctct    4800
tcacggcgat ctatgcggct tctataacaa cgtggaacgg gtgggcatgg attgcaggcg    4860
ctgccctcta cttgctctgc ctgccggcgc tgcgtcgcgg gctttggagc ggcgcagggc    4920
aacgagccga tcgctgatcg tggaaacgat aggcctatgc catgcgggtc aaggcgactt    4980
ccggcaagct atacgcgccc taggagtgcg gttggaacgt tggcccagcc agatactccc    5040
gatcacgagc aggacgccga tgatttgaag cgcactcagc gtctgatcca agaacaacca    5100
tcctagcaac acggcggtcc ccgggctgag aaagcccagt aaggaaacaa ctgtaggttc    5160
gagtcgcgag atccccggga accaaaggaa gtaggttaaa cccgctccga tcaggccgag    5220
ccacgccagg ccgagaacat tggttcctgt aggcatcggg attggcggat caaacactaa    5280
agctactgga acgagcagaa gtcctccggc cgccagttgc caggcggtaa aggtgagcag    5340
aggcacggga ggttgccact tgcgggtcag cacggttccg aacgccatgg aaaccgcccc    5400
cgccaggccc gctgcgacgc cgacaggatc tagcgctgcg tttggtgtca acaccaacag    5460
cgccacgccc gcagttccgc aaatagcccc caggaccgcc atcaatcgta tcgggctacc    5520
tagcagagcg gcagagatga acacgaccat cagcggctgc acagcgccta ccgtcgccgc    5580
gaccccgccc ggcaggcggt agaccgaaat aaacaacaag ctccagaata gcgaaatatt    5640
aagtgcgccg aggatgaaga tgcgcatcca ccagattccc gttggaatct gtcggacgat    5700
catcacgagc aataaacccg ccggcaacgc ccgcagcagc ataccggcga cccctcggcc    5760
tcgctgttcg ggctccacga aaacgccgga cagatgcgcc ttgtgagcgt ccttggggcc    5820
gtcctcctgt ttgaagaccg acagcccaat gatctcgccg tcgatgtagg cgccgaatgc    5880
cacggcatct cgcaaccgtt cagcgaacgc ctccatgggc ttttttctcct cgtgctcgta    5940 aacggacccg aacatctctg gagctttctt cagggccgac aatcggatct cgcggaaatc    6000
ctgcacgtcg gccgctccaa gccgtcgaat ctgagcctta atcacaattg tcaattttaa    6060
tcctctgttt atcggcagtt cgtagagcgc gccgtgcgtc ccgagcgata ctgagcgaag    6120
caagtgcgtc gagcagtgcc cgcttgttcc tgaaatgcca gtaaagcgct ggctgctgaa    6180 ccccagccg gaactgaccc cacaaggccc tagcgtttgc aatgcaccag gtcatcattg    6240
acccaggcgt gttccaccag gccgctgcct cgcaactctt cgcaggcttc gccgacctgc    6300
tcgcgccact tcttcacgcg ggtggaatcc gatccgcaca tgaggcggaa ggtttccagc    6360
```

```
ttgagcgggt acggctcccg gtgcgagctg aaatagtcga acatccgtcg ggccgtcggc    6420
gacagcttgc ggtacttctc ccatatgaat ttcgtgtagt ggtcgccagc aaacagcacg    6480
acgatttcct cgtcgatcag gacctggcaa cgggacgttt tcttgccacg gtccaggacg    6540
cggaagcggt gcagcagcga caccgattcc aggtgcccaa cgcggtcgga cgtgaagccc    6600
atcgccgtcg cctgtaggcg cgacaggcat tcctcggcct tcgtgtaata ccggccattg    6660
atcgaccagc ccaggtcctg gcaaagctcg tagaacgtga aggtgatcgg ctcgccgata    6720
ggggtgcgct tcgcgtactc caacacctgc tgccacacca gttcgtcatc gtcggcccgc    6780
agctcgacgc cggtgtaggt gatcttcacg tccttgttga cgtggaaaat gaccttgttt    6840
tgcagcgcct cgcgcgggat tttcttgttg cgcgtggtga cagggcaga gcgggccgtg    6900 tcgtttggca tcgctcgcat cgtgtccggc acggcgcaa tatcgaacaa ggaaagctgc    6960
atttccttga tctgctgctt cgtgtgtttc agcaacgcgg cctgcttggc ctcgctgacc    7020
tgttttgcca ggtcctcgcc ggcggttttt cgcttcttgg tcgtcatagt tcctcgcgtg    7080
tcgatggtca tcgacttcgc caaacctgcc gcctcctgtt cgagacgacg cgaacgctcc    7140
acggcggccg atggcgcggg cagggcaggg ggagccagtt gcacgctgtc gcgctcgatc    7200
ttggccgtag cttgctggac catcgagccg acggactgga aggtttcgcg gggcgcacgc    7260
atgacggtgc ggcttgcgat ggtttcggca tcctcggcgg aaaacccgc gtcgatcagt    7320 tcttgcctgt atgccttccg gtcaaacgtc cgattcattc accctccttg cgggattgcc    7380
ccgactcacg ccggggcaat gtgcccttat tcctgatttg acccgcctgg tgccttggtg    7440
tccagataat ccaccttatc ggcaatgaag tcggtcccgt agaccgtctg gccgtccttc    7500
tcgtacttgg tattccgaat cttgccctgc acgaatacca gcgacccctt gcccaaatac    7560
ttgccgtggg cctcggcctg agagccaaaa cacttgatgc ggaagaagtc ggtgcgctcc    7620
tgcttgtcgc cggtcgtggc cgcgccaacc tttgcgatcc gcaagcgcgc ggtcgccatc    7680
ttcacgctgg aacagtacgt cgaggcgggc atcatgaccc gcgagcaata cgaggtcatt    7740
aaaagcgccg tgattgatga tatagcggcc cggctgctcc tggttctcgc gcaccgaaat    7800
gggtgacttc accccgcgct ctttgatcgt ggcaccgatt tccgcgatgc tctccgggga    7860
aaagccgggg ttgtcggccg tccgcggctg atgcggatct tcgtcgatca ggtccaggtc    7920
cagctcgata gggccggaac cgccctgaga cgccgcagga gcgtccagga ggctcgacag    7980
gtcgccgatg ctatccaacc ccaggccgga cggctgcgcc gcgcctgcgg cttcctgagc    8040
ggccgcagcg gtgttttcct tggtggtctt ggcttgagcc gcagtcattg ggaaatctcc    8100
atcttcgtga acacgtaatc agccagggcg cgaacctctt tcgatgcctt gcgcgcggcc    8160
gttttcttga tcttccagac cggcacaccg gatgcgaggg catcggcgat gctgctgcgc    8220
aggccaacgg tggccggaat catcatcttg gggtacgcgg ccagcagctc ggcttggtgg    8280
cgcgcgtggc gcggattccg cgcatcgacc ttgctgggca ccatgccaag gaattgcagc    8340
ttggcgttct tctggcgcac gttcgcaatg gtcgtgacca tcttcttgat gccctggatg    8400
ctgtacgcct caagctcgat gggggacagc acatagtcgg ccgcgaagag gcggccgcc    8460 aggccgacgc caagggtcgg ggccgtgtcg atcaggcaca cgtcgaagcc ttggttcgcc    8520
agggccttga tgttcgcccc gaacagctcg cgggcgtcgt ccagcgacag ccgttcggcg    8580
ttcgccagta ccgggttgga ctcgatgagg gcgaggcgcg cggcctggcc gtcgccggct    8640
gcgggtgcgg tttcggtcca gccgccggca gggacagcgc cgaacagctt gcttgcatgc    8700
aggccggtag caaagtcctt gagcgtgtag gacgcattgc cctgggggtc caggtcgatc    8760
```

```
acggcaaccc gcaagccgcg ctcgaaaaag tcgaaggcaa gatgcacaag ggtcgaagtc      8820
ttgccgacgc cgcctttctg gttggccgtg accaaagttt tcatcgtttg gtttcctgtt      8880
ttttcttggc gtccgcttcc cacttccgga cgatgtacgc ctgatgttcc ggcagaaccg      8940
ccgttacccg cgcgtacccc tcgggcaagt tcttgtcctc gaacgcggcc cacacgcgat      9000
gcaccgcttg cgacactgcg cccctggtca gtcccagcga cgttgcgaac gtcgcctgtg      9060
gcttcccatc gactaagacg ccccgcgcta tctcgatggt ctgctgcccc acttccagcc      9120
cctggatcgc ctcctggaac tggctttcgg taagccgttt cttcatggat aacacccata      9180
atttgctccg cgccttggtt gaacatagcg gtgacagccg ccagcacatg agagaagttt      9240
agctaaacat ttctcgcacg tcaacacctt tagccgctaa aactcgtcct tggcgtaaca      9300
aaacaaaagc ccggaaaccg ggctttcgtc tcttgccgct tatggctctg cacccggctc      9360
catcaccaac aggtcgcgca cgcgcttcac tcggttgcgg atcgacactg ccagcccaac      9420
aaagccggtt gccgccgccg ccaggatcgc gccgatgatg ccggccacac cggccatcgc      9480
ccaccaggtc gccgccttcc ggttccattc ctgctggtac tgcttcgcaa tgctggacct      9540
cggctcacca taggctgacc gctcgatggc gtatgccgct tctccccttg gcgtaaaacc      9600
cagcgccgca ggcggcattg ccatgctgcc cgccgctttc ccgaccacga cgcgcgcacc      9660
aggcttgcgg tccagacctt cggccacggc gagctgcgca aggacataat cagccgccga      9720
cttggctcca cgcgcctcga tcagctcttg cactcgcgcg aaatccttgg cctccacggc      9780
cgccatgaat cgcgcacgcg gcgaaggctc cgcagggccg                            9820
```

US 8,455,231 B2

CELL-FREE SYSTEM FOR SYNTHESIZING MEMBRANE PROTEINS CELL FREE METHOD FOR SYNTHESIZING MEMBRANE PROTEINS

PRIORITY CLAIM

This utility application claims the benefit of U.S. Provisional Patent Application No. 61/150,436, filed on Feb. 6, 2009.

CONTRACTUAL ORIGIN OF THE INVENTION

The U.S. Government has rights in this invention pursuant to Contract No. AC02-06CH11357 between the U.S. Department of Energy and UChicago Argonne, LLC.

BACKGROUND OF THE INVENTION

1. Field of the Invention

This invention relates to a system and method for producing proteins, and more particularly this invention relates to a cell-free system and cell-free method for producing and maintaining heterologous membrane proteins in their native forms.

2. Background of the Invention

The cell membrane serves as the interface between an organism and its environment, and internal membranes in eukaryotic organisms separate functional compartments within cells. Proteins inserted in these membranes carry out the essential functions of the cell: biological processes such as uptake of nutrients, excretion of wastes, generation of energy, and signal transduction.

The functions performed by membrane proteins are extremely important for all organisms. Despite the fact that membrane proteins represent approximately 30% of every genome and comprise more than 60% of all drug targets, only about 100 unique membrane protein structures have been determined to date, in contrast with unique structures representing approximately 10,000 soluble protein families.

A major factor influencing the paucity of membrane protein structures is that the expression levels of membrane proteins in native tissue are generally low. While many membrane proteins have been isolated in functional form from their native host organisms, purification in such cases is highly protein-specific, is not adaptable to high-throughput methodologies, and rarely yields the amounts of pure membrane proteins that are needed for extensive biochemical studies and crystallization trials.

Since the natural abundance of many membrane proteins is low and the purification process is daunting, recombinant systems are often employed now to overexpress membrane proteins. *Escherichia* (*E.*) *coli*-based systems are used most commonly for the heterologous expression of soluble proteins, as they offer many advantages such as simplicity, low cost and rapid growth. They suffer limitations, however, especially when applied to the expression of non-*E. coli* membrane proteins. Significantly, native *E. coli* strains do not have adequate space in their membranes to accommodate heterologously-expressed membrane proteins, as noted in Arechaga, I., Miroux, B., Karrasch, S., Huijbregts, R., de Kruijff, B., Runswick, M. J., and Walker, J. E. (2000) "Characterization of new intracellular membranes in *Escherichia coli* accompanying large scale over-production of the b subunit of F(1)F(o) ATP synthase." *FEBS Letters* 482, 215-219, and Miroux, B., and Walker, J. E. (1996) "Over-production of proteins in *Escherichia coli*: Mutant hosts that allow synthesis of some membrane proteins and globular proteins at high levels." *Journal of Molecular Biology* 260, 289-298.

Because the host cell's own membrane proteins already occupy a defined proportion of the cell's membranes, the availability of any remaining membrane space severely limits the absolute number of copies of the target protein which can be properly inserted into the cell membranes.

In addition, a high level of expression in *E. coli* can saturate the secretory machinery for integration of the heterologous protein into the membrane, often resulting in cell death, degradation of the target protein, or precipitation of the heterologously-expressed membrane protein as inclusion bodies (insoluble aggregates within cells). (Kiefer et al., Biochemical Society Transactions 27, 908-912 (1999); Korepanova et al., Protein Science 14:148-158 (2005); and Columbus et al., Protein Science 15:961-975 (2006).

Overall success of an in vivo *Rhodobacter* membrane protein expression system is encouraging, per U.S. Pat. No. 6,465,216 awarded to the inventors on Oct. 15, 2002, and incorporated herein by reference. However, the inventors have observed that expression of some target proteins has a negative impact on cell growth rate. Also, some target membrane proteins are expressed early in the auto-induction process but then disappear as the cell density increases, suggesting proteolysis.

Many eukaryotic protein expression systems are also available and have been employed for the production of membrane proteins. However, they suffer from many of the same limitations and are cumbersome and expensive for the preparation of the quantities of membrane proteins that are necessary for structure determination experiments.

*Rhodobacter* (*R.*) cell free extracts also have been used to produce native membrane proteins, as reported in Troschel D, Eckhardt S, Hoffschulte H K and Muller M (1992) Cell-free synthesis and membrane integration of the reaction center subunit H from *Rhodobacter capsulatus*. FEMS Microbiol Lett 91:129-133. However, these proteins were localized to *Rhodobacter* ICM vesicles if (and only if) the vesicles were added cotranslationally; that is, the ICM must be present during protein synthesis for efficient membrane incorporation. More importantly, *Rhodobacter* extracts have not been used to produce heterologous proteins.

The need exists in the art for a cell-free system and method which enables production of significant quantities of heterologous membrane proteins in functional form. The system and method should be compatible with all subsequent steps of sequestration, solubilization, stabilization and purification of the target membrane protein.

SUMMARY OF THE INVENTION

An object of the present invention is to provide a cell-free system and a cell-free method for producing proteins that overcomes many of the disadvantages of the prior art.

Another object of the present invention is to provide a cell-free method for producing heterologous membrane proteins. A feature of the invention is the cell-free production of the membrane proteins utilizing a coupled transcription/translation system. The advantage of this embodiment of the invention is eliminating the need for a separate step of generating mRNA.

Still another object of the present invention is a cell-free method for producing membrane proteins in *Rhodobacter* extracts. A feature of the invention is the use of intracytoplasmic membranes (ICM) of *Rhodobacter* to simultaneously receive and encapsulate the target proteins during the latter's production. The amount of host protein normally present in the ICM vesicles is reduced by deletions of genes encoding host protein which are not essential for cell growth. An advantage of the invention is that larger amounts of target protein can be sequestered in the vesicles which are formed in the deletion strains inasmuch as the vesicles are devoid of some fraction of the native protein complement.

Another object of the present invention is to provide a cell-free method for producing heterologous proteins that associate with membrane for proper folding or function. A feature of the invention is that the membrane is derived from an organism which is engineered such that it does not express protein considered non-essential to the formation of membrane. For example, if the organism is a photosynthetic organism, the genome of the organism is modified such that formation of its intracytoplasmic membrane is devoid of light harvesting antenna and/or reaction centers of the photosynthetic apparatus, and other non-membrane forming proteins. An advantage is that the space ultimately defined by the membrane is optimized to encapsulate maximal amounts of the heterologous proteins.

Yet another object of the present invention is to provide a cell-free method for producing heterologous soluble proteins which interact with membrane-associated protein for assembly into an oligomeric complex. A feature of the invention is that the presence of membranes promotes folding of the soluble proteins. Within the invented system, the soluble proteins are localized to aqueous phases.

Briefly, the invention provides an in vitro method for producing proteins, the method comprising selecting organisms which naturally produce intracytoplasmic membranes; modifying DNA of the organisms by deleting non-essential functions of the organism not associated with the formation of the intracytoplasmic membranes, expressing the modified DNA to create modified intracytoplasmic membranes, fractionating cells of such organisms to obtain quantities of intracytoplasmic membranes and; mixing the modified intracytoplasmic membranes with DNA or RNA templates that encode the target proteins and with a transcription/translation-competent cellular extract to cause simultaneous production of the proteins and their encapsulation within the intracytoplasmic membranes.

A specific embodiment of the invention provides an in vitro method for producing heterologous proteins, the method comprising supplying intracytoplasmic membranes prepared from an organism modified to delete genes encoding non-essential proteins of the intracytoplasmic membranes, such that the deletion does not inhibit production of the membranes; providing a suitable expression vector or DNA segment encoding heterologous protein; and mixing the intracytoplasmic membranes with the expression vector or DNA segment template and a transcription/translation-competent cellular extract to cause simultaneous production and encapsulation of the heterologous proteins within the intracytoplasmic membranes.

The invention also provides a method for simultaneously producing and sequestering protein, the method comprising selecting organisms which naturally produce intracytoplasmic membranes; modifying DNA of the organisms by deleting genes encoding non-essential functions of the organism to yield intracytoplasmic membranes with reduced protein content; culturing the modified organism to express modified intracytoplasmic membranes; and mixing the modified intracytoplasmic membranes with DNA templates or RNA templates that encode the protein so as to cause simultaneous production of the protein and encapsulation of the protein within the intracytoplasmic membranes.

BRIEF DESCRIPTION OF THE DRAWING

The foregoing and other objects, aspects and advantages of this invention will be better understood from the following detailed description of the preferred embodiments of the invention with reference to the drawing, in which:

FIG. 5A-J are vectors adapted to receive template DNA, in accordance with features of the present invention;

DETAILED DESCRIPTION OF THE INVENTION

The use of *Rhodobacter* is an avenue for in vivo production of proteins. A major advantage for expression of proteins in *Rhodobacter* is that expressed proteins are localized to that organism's intracyto-plasmic membrane (ICM). This attribute indicates that expressed proteins assume a structure that facilitates proper insertion into the membrane.

The inventors have developed robust mixtures of components of intracytoplasmic membrane-producing bacteria, optimized generically, for a diverse range of applications. Specifically, the inventors have determined the components necessary to define a robust cell-free system employing *Rhodobacter* ICMs that can be applied generically for the heterologous production of a wide variety of membrane proteins. The invented cell-free protocol essentially provides an open reactor to which reactants can be added and removed. In an embodiment of the invented system, the open reactor is comprised of membranes defining vesicles or sheets, fragments of membranes, or combinations of these protein encapsulating/capturing structures defining surfaces, and other configurations.

The present invention produces membrane proteins, membrane-associated proteins that utilize membrane association for structural integrity and/or function, and soluble proteins that interact with membrane-associated proteins for oligomeric assembly or that require association with the membrane for proper folding. The invention enables the production and encapsulation of different target proteins into the same vesicle either simultaneously or serially. For example, the system enables first the production of chaperone proteins which will help proper folding of subsequently produced proteins.

The invented cell-free protocol is an open and controllable system, which is to say that the protocol is amenable to the addition of small or large molecules not endogenous to the *Rhodobacter* extract that can enhance its performance or lead to production of the desired type of membrane proteins. "Small" molecules include cofactors required by the target protein, labeled or unnatural amino acids, and tRNAs. Examples of "large" molecules include chaperones, other template DNAs encoding additional subunits of a hetero-oligomeric complex or maturation proteins required for cofactor assembly, and membrane fragments. One possible outcome is first, the production of a membrane-integral protein which presents itself as protruding from the membrane vesicle, and then second, the production of another protein which attaches to the first protein.

The cell-free protein production method shares target membrane protein types, donor organisms for intracytoplasmic membranes and their genomes, and some wet chemistry techniques with the in vivo method described in U.S. Pat. No. 6,465,216, issued on Oct. 15, 2002 and incorporated herein by reference.

Figure 1:
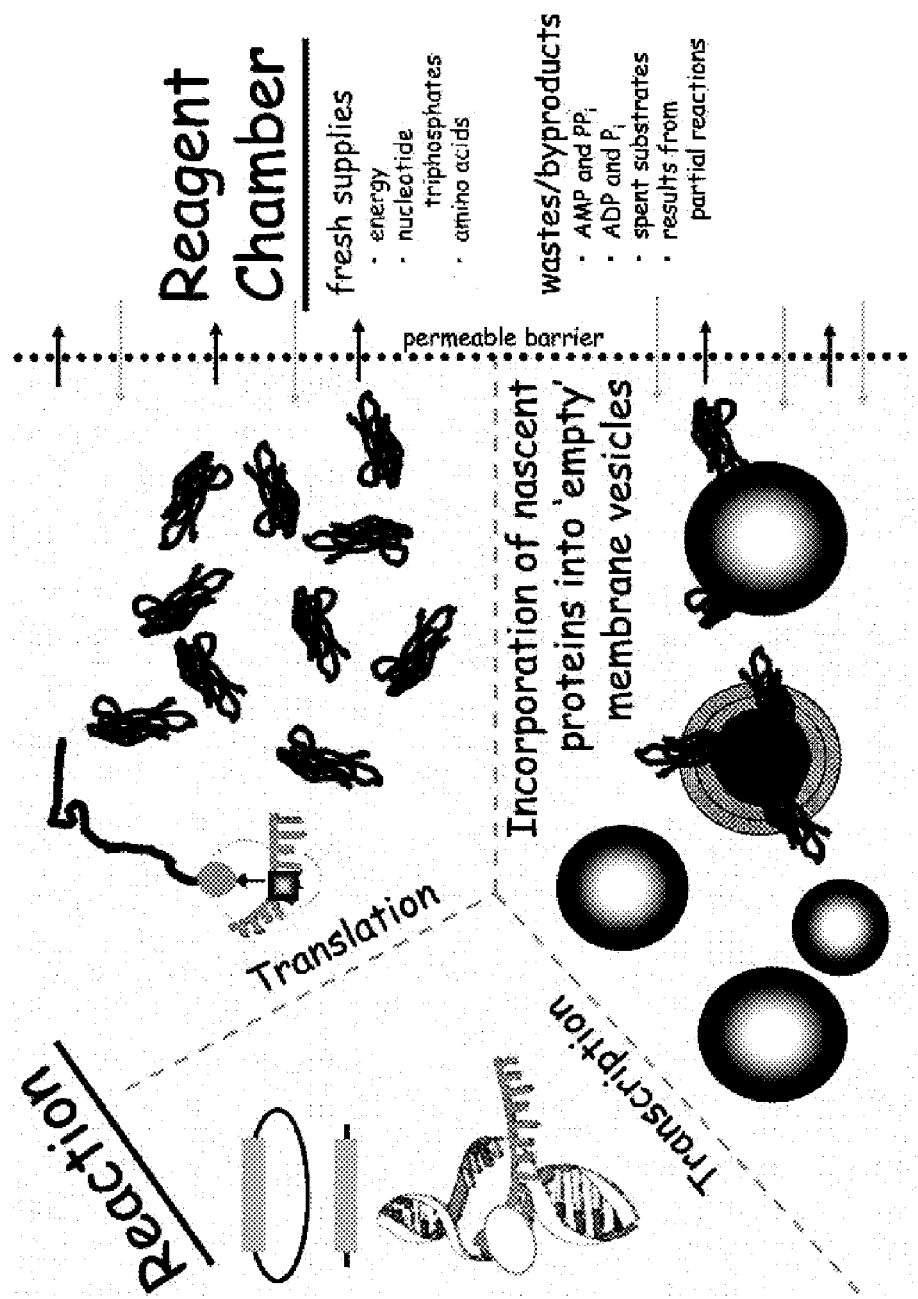
FIG. 1 is a schematic view of the invented method and system, in accordance with features of the present invention.

An embodiment of the invented cell-free protein production system is schematically depicted in FIG. 1. Cell-free production of membrane proteins with *Rhodobacter* extracts occurs via a coupled transcription/translation system. The in vitro synthesis of membrane proteins and their immediate incorporation into lipid bilayers occurs via the combination of separate and distinct preparations from *Rhodobacter* strains: (i) an endogenous extract containing RNA polymerase and ribosomes couples translation of proteins with transcription of mRNAs from PCR amplicons or plasmid DNA housing the target gene, and (ii) membrane vesicles from *Rhodobacter* hosts deleted for proteins of the photosynthetic apparatus are used as the storage medium for nascent, natively-folded membrane proteins. The latter would denature and precipitate rapidly in the absence of a compatible, stabilizing environment.

Soluble and membrane-containing extracts are isolated easily by differential centrifugation of lysates from cells of wild-type or engineered *Rhodobacter* strains. In production mode, a reagent chamber is utilized to provide a fresh supply of critical reaction components and to remove wastes and byproducts that inhibit transcription and translation.

A feature of this coupled transcription/translation system is isolated, relatively protein-free, membrane vesicles that can be added to the reaction and that can be used to incorporate the large amount of heterologous membrane protein being produced. This enables the inexpensive production of milligram quantities of proteins for structural and functional studies. For example, yields of membrane protein using the invented protocol are predicted to be between about 0.01 mgs/ml and 2 mgs/ml of extract liquor. Embodiments of the system typically yield at least about 0.5 mgs of protein per ml of extract liquor.

In one embodiment, the mixture presented in Table 1, infra is utilized to produce the cell-free proteins.

Coupling the invented protocol with continuous reaction-type approaches (using dialysis membranes or continuous feed approaches available commercially), provides an inexpensive production of milligram quantities of membrane proteins for structural and functional studies. Several versions of a cell-free *Rhodobacter*-based expression system for membrane proteins are enabled, with scales geared individually towards preparative, high-throughput screening, or labeling applications.

For the sake of illustration, the genome of the *R. sphaeroides* expression system is adapted herein to facilitate the cell-free production of membrane proteins in native form. However, any organism which produces intracellular membranes is a suitable source of intracellular membranes to be manipulated as described herein. Species belonging to the following families and their respective genera are suitable for the instant method:

| Green sulfur bacteria |
| --- |
| *Chlorobium* |
| *Prosthecochloris* |
| *Ancalochloris* |
| *Pelodictyon* |
| *Chloroherpeton* |
| Purple and Green bacteria |
| *Thiospirillum* |
| *Thiorhodovibrio* |
| *Blastochloris* |
| *Chromatium* |
| *Thiocystis* |
| *Lamprocystis* |
| *Lamprobacter* |
| *Thiodictyon* |
| *Amoebobacter* |
| *Thiopedia* |
| *Thiocapsa* |
| *Ectothiorhodospira* |
| *Rhodospirillum* |
| *Rhodopila* |
| *Rhodomicrobium* |
| *Rhodobacter* |
| *Rhodopseudomonas* |
| *Rhodocyclus* |
| *Rhodoferax* |
| *Rubrivivax* |
| *Heliobacter* |
| *Heliobacter* |
| Filamentous Anoxygenic Phototrophs |
| *Chloroflexus* |
| Marine *Chloroflexus*-like organisms |
| *Heliothrix* |
| *Chloronema* |
| *Oscillochloris* |
| Aerobic Anoxygenic Phototrophs |
| *Eythrobacter* |
| *Roseobacter* |
| *Methylobacterium* |
| *Porphyrobacter* |
| *Rhizobium* |
| *Acidiphilium* |
| *Erythromicrobium* |
| *Roseococcus* |

*Rhodobacter* ICM
Discussion

*Rhodobacter*'s ICMs provide a well-defined hydrophobic destination for co- or post-translational insertion of expressed membrane proteins in in vitro applications. Without a requirement for detergent to maintain protein solubility, a *Rhodobacter* cell-free expression system containing membrane fragments avoids all the deleterious side-effects that detergents bring to the reaction mixture. Both the S135 extract as well as ICM preparations are stable in an ultra-low freezer (say at −80° C.) for extended periods (a year or more), and can be used to prepare a kit for cell-free expression of heterologous membrane proteins.

The following two strains of *R. sphaeroides* were evaluated as a source of intracytoplasmic membrane:
1. wild-type ATCC17023 (RC$^+$LHI$^+$LHII$^+$; PS$^+$;
2. ΔΔ11 ATCC PTA-5921 [RC$^-$LHI$^-$LHII$^-$; PS$^-$; (Pokkuluri et al., 2002)].

These strains differ in both the nature and number of native complexes of the photosynthetic apparatus present in the ICM.

Plasmid Vector Detail

Figure 5G:
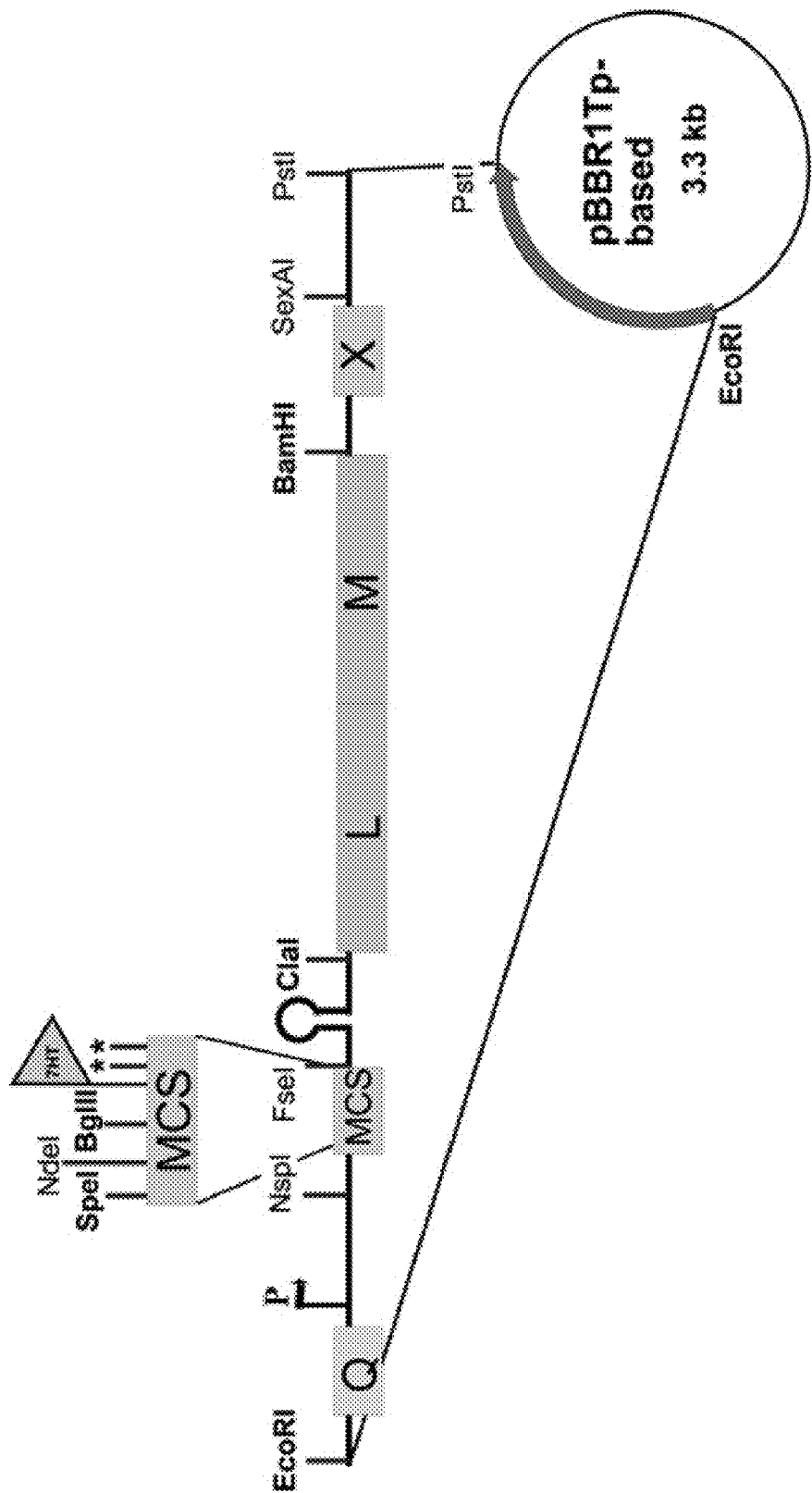
Figure 5H:
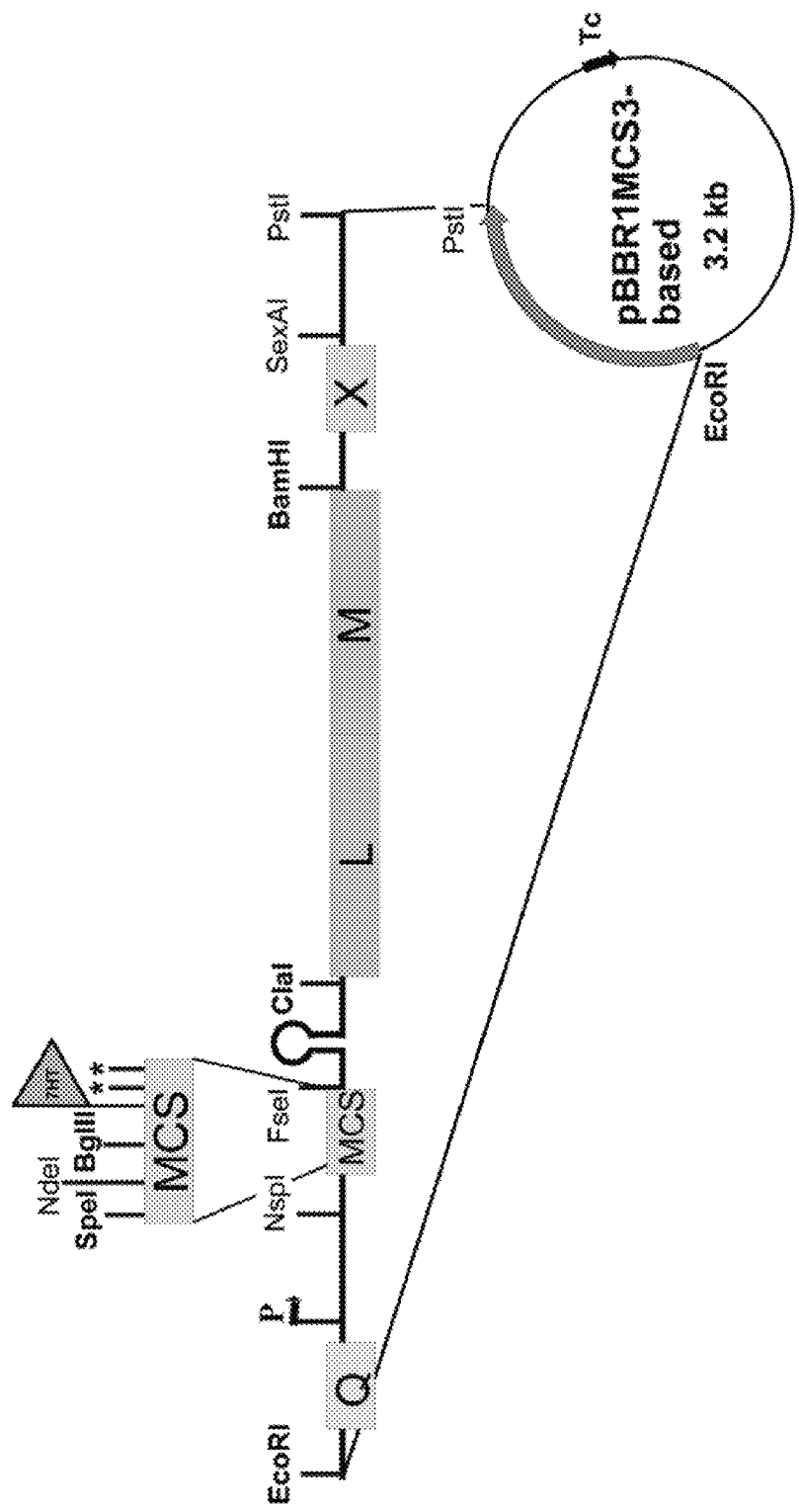

A suite of plasmids has been constructed for insertion of foreign genes downstream of promoters that direct synthesis of the photosynthetic apparatus. Exemplary plasmid vectors are disclosed herein as group FIG. 5.

Figure 10:
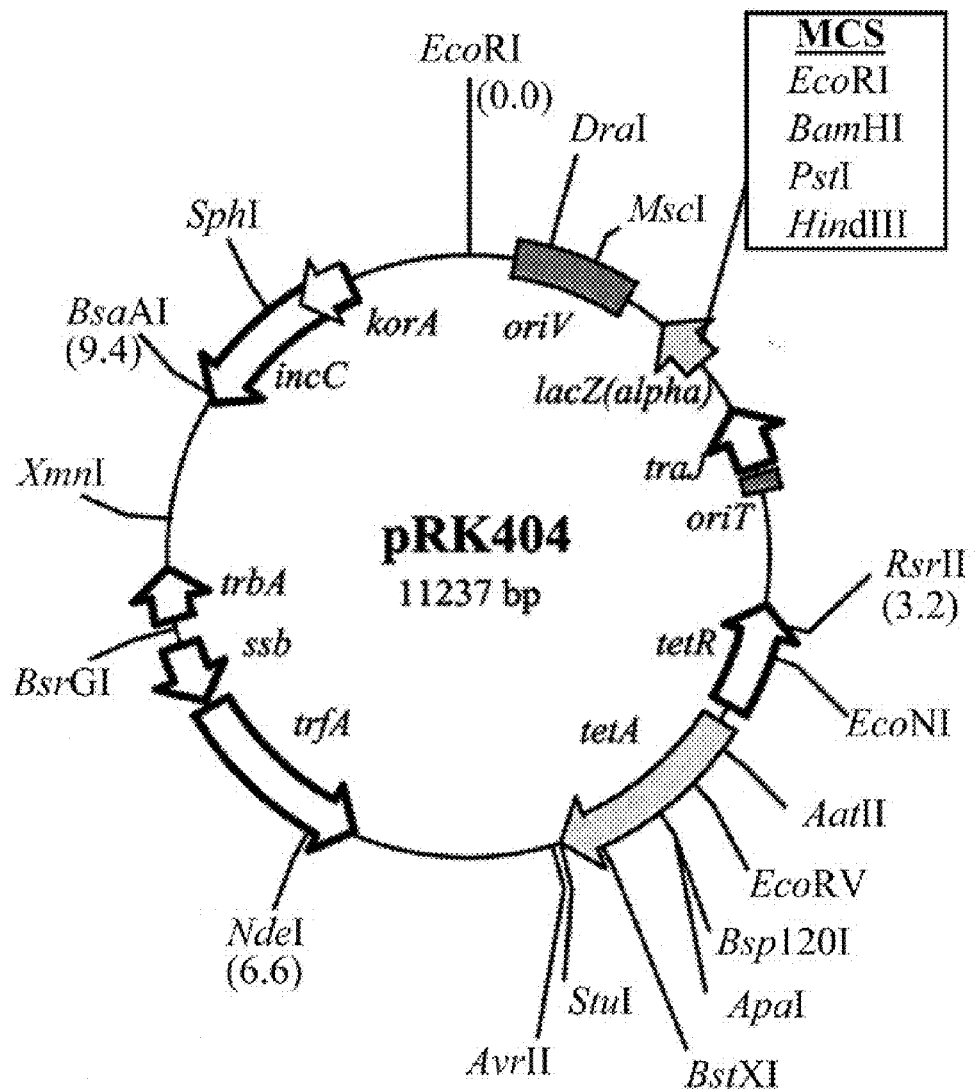
FIG. 10 is a map of the broad-host-range plasmid pRK404.
Figure 11:
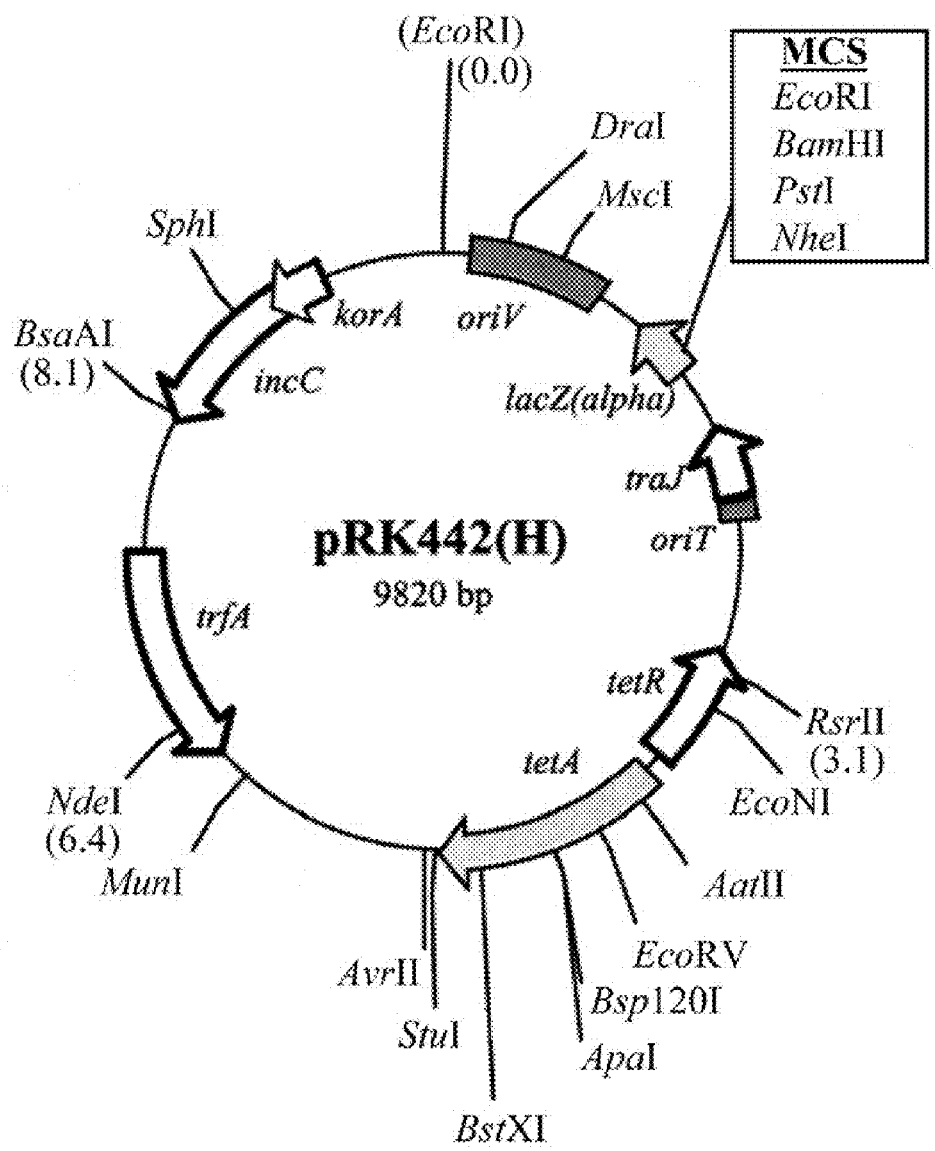
FIG. 11 is a map of the broad-host-range plasmid pRK 442.

All of the vectors utilized to date in the cell free reactions are derivatives of broad-host-range plasmid pRK404 (FIG. 5A-C, F-H), and plasmid pRK 442(H), depicted herein as FIGS. 10 and 11, respectively, and disclosed in its entirety in Scott et al., "Sequences of versatile broad-host-range vectors of the RK2 family." *Plasmid* 50: 74-79. (2003), which is incorporated herein by reference. The selection of these plasmids is for illustration only inasmuch as other plasmids are also suitable vectors. The complete sequences of the aforementioned exemplary plasmids are well known and available publically, including at the U.S. National Institutes of Health. For illustration purposes, the sequence listing for exemplary plasmids (pRK404 and pRK442(H)) found at that website, is also attached to the end of this specification.

A broad-host-range functionality is not a requirement for the cell-free system because replication is not necessary. Foreign genes are placed under control of the oxygen- and/or light-regulated puf ($P_{puf}$) or puc ($P_{puc}$) promoters. A region of stable RNA secondary structure (hairpin) dictates the stability of the upstream transcript. Vectors encode a C-terminal heptahistidine tag (HT) that is fused in frame with two stop codons (*). Vector d encodes an N-terminal membrane anchor/linker domain and Vector e provides an N-terminal signal sequence. Foreign genes are inserted via the SpeI and BgIII sites in Vectors a-e; Vector f carries a PmlI site that enables ligation-independent cloning. (a) pRKPLHT4; (b) pRKPLHT1; (c) pRKPLHT7; (d) pRKMAHT1; (e) pRKSSHT1; (f) pRKLICHT1.

FIGS. 5G-J depict smaller platform vectors for the *Rhodobacter* expression system, based on the series of broad-host-range vectors derived from pBBR1, for a plasmid encoding tetracycline resistance (g) or trimethoprim resistance (h).

Other expression vectors (FIG. 5*d, e*) were constructed to facilitate membrane incorporation of foreign proteins expressed in *Rhodobacter* ICM extract. To ensure that the target protein will be targeted to the intracytoplasmic membrane, gene segments encoding peptides which perform this function in *R. sphaeroides* are appended to the vector. Specifically, the pRKPLHT1 platform vector was modified to incorporate either the cleavable signal sequence from a periplasmic cytochrome or the N-terminal membrane anchor/linker domain derived from cytochrome cy of *R. capsulatus*. This membrane-bound cytochrome is expressed heterologously to high levels as described in the literature. The segment encoding the membrane anchor located immediately upstream of cycY was synthesized as an oligonucleotide cassette that included ends for restriction site AvrII at the 5' end and BglII at the 3' end. The resulting cassette was cloned into pRKPLHT1. Additional details related to the heterologous expression of membrane-bound cytochrome is found in Myllykallio, H., et al., Cytochrome cy of *Rhodobacter capsulatus* is attached to the cytoplasmic membrane by an uncleaved signal sequence-like anchor. J Bacteriol, 1997. 179(8): p. 2623-31, incorporated herein by reference.

If ICM synthesis would benefit the functional expression of the membrane protein complex, polycistronic DNA segments are inserted into existing vectors where synthesis is driven by either the puf or puc promoters. In this case, stoichiometric amounts of proteins would be produced from the operon (unless inherent regulatory elements dictating otherwise are present and are recognized by *Rhodobacter*). Another vector in this series has been constructed which allows for dual expression of two or more foreign genes—in different relative stoichiometries—by replacement of both the LHI and RC coding regions. Two considerations drive the latter strategy: (1) the function of many multi-subunit protein complexes often requires a subunit ratio other than 1:1 and (2) maturation proteins would be required in catalytic amounts, whereas overexpression of structural subunit(s) of the target complex would be desired.

In one invented embodiment, a plasmid that enables expression of two or more heterologous genes has been constructed by combining the engineering for pRKPLHT1 (FIG. 5*b*) with the engineering for pRKPLHT4 (FIG. 5*a*). In brief, a ClaI-SexAI segment of pRKPLHT1 was replaced with a synthesized oligonucleotide cassette that carries a second multiple-cloning site region whereby a second gene or set of genes can be cloned via unique XbaI and BamHI sites. Fragments with these cohesive ends could be cloned into either multiple-cloning-site region of the dual expression vector.

ICM Preparation Detail

Intracytoplasmic membrane vesicles (chromatophores) were prepared by using a French press (SLM Aminco) as described previously in the presence of the protease inhibitors Pefaploc SC, leupeptin, and Pepstatin A as recommended by the manufacturer (Roche).). Spheroplasts were prepared by treatment of cells with 10 mgs/ml lysozyme in an osmotically stabilized solution (infra). Outside-out vesicles were prepared from spheroplasts by mechanical lysis or by simple dilution. Membrane sheets were isolated from lysozyme-treated cells by osmotic lysis in 10 mM K2PO4 (pH 7.4)-2 mM EDTA-0.1 mM phenylmethylsulfonyl fluoride (PMSF) buffer.

Once the lysis was complete, catalytic amounts of DNAse (suchas commercially provided from such manufacturers as Signma Chemical Co.) and 10 mM $MgCl_2$ were added, and mixing continued for 60 min at 48 C. Membrane sheets were isolated by centrifugation at 25,000×3 g for 20 min and washed once in the above-described buffer.

Engineered ICM
Structure Detail

The effect of deletion of native transmembrane complexes on the morphology and volume of the ICM was examined by transmission electron microscopy. In the wild-type organism, the ICM appears as vesicles. The morphology of the ICM changes, however, as its protein content is manipulated. Deletion of the LHII complex of *R. sphaeroides* yields a strain characterized by tubular membranes. Strains that synthesize the LHI and LHII complexes, but carry a deletion of the RC, look much like the native strain, and a strain lacking all three complexes of the photosynthetic apparatus (ΔΔ11) is characterized by a less structured ICM that is neither tubes nor spheres.

This specialized membrane is contiguous with the cytoplasmic membrane, but differs from the latter in its chemical and protein com-position, its morphological and physical properties, and in its kinetics of biogenesis. Upon cell lysis via mechanical breakage (e.g., French press, microfluidizer), the ICM invaginations break apart from the cytoplasmic membrane, becoming sealed inside out vesicles. Following the initial removal of cell debris, these vesicles are isolated easily by differential centrifugation. In the native organism, this fraction is rich in the integral membrane proteins that constitute the photosynthetic apparatus. In engineered expression strains strains used for in vivo expression of membrane proteins, this fraction should contain the heterologous membrane protein, and its cellular localization can be tracked easily by using the polyhistidine tag.

The inventors found that ICM derived from ΔΔ11 incorporated the highest yield overall of target protein. Yields of more than 20 mg/L of target membrane protein have been obtained when employing the ΔΔ11 host strain for in vivo expression in Rhodobacter utilizing chemoheterotrophic culture conditions Detection/Quantitation
Detail of Expressed Proteins To determine whether the foreign membrane protein is incorporated into the ICM, membranes from the reaction mixture are analyzed by SDS-PAGE and immunoblotting techniques. Success in expressing a target membrane protein is measured by comparing the immuno-blot signal from the target protein with that of a positive control protein.

The screening process includes determination of whether the foreign membrane proteins are incorporated into the ICM. The immunoblot methods employed also report whether any his-tagged proteins are present in inclusion bodies (or other high-molecular-weight aggregates) or whether any have been cleaved by proteases. The small amount of target protein that is found in the soluble fraction results from small membrane fragments that do not pellet during ultracentrifugation. Centrifugation of greater duration or force pellets these small ICM vesicles quantitatively (data not shown). ICM localization of the expressed foreign protein is taken as an indicator that the protein possesses at least some degree of structural integrity that directs membrane insertion.

Target Protein
Selection Detail

A myriad of proteins is suitable for cell-free production and simultaneous sequestration with ICM systems. This cell-free expression system can be applied for the production of proteins that encompass all three kingdoms of life.

Membrane proteins selected for initial testing of the cell-free system were members of the E. coli membrane proteome, spanned a range of molecular weights, number of transmembrane passes, and isoelectric points, and were known to be expressed to high levels (greater than 10 mgs/liter of cell culture) in ICM in the cell-based system.

Detail of Purification of Expressed Membrane Proteins from the Rhodobacter ICM.

Generic, reproducible and rapid methods have been developed for solubilizing and purifying expressed proteins from the membranes of Rhodobacter. sphaeroides. Utilizing the polyhistidine tag engineered into the expression vector, detergent-solubilized target membrane proteins can be purified readily by IMAC. This method is specific, its rapidity can facilitate purification of the target protein in its native state, and its general utility eliminates the need to determine de novo the type of chromatography which will be successful for each protein.

By combining affinity chromatography sequentially with gel filtration and ion exchange steps, highly purified heterologously-expressed target proteins can be recovered rapidly from ICMs.

Modification Detail to make Rhodobacter More User-Friendly as a Source of a Transcription/Translation-Competent Cell-Free Extract To make the Rhodobacter extract expression system more accommodating to foreign genes, engineering was conducted to remove enzymatic activities that interfere with uptake and maintenance of exogenous DNA, and the accumulation and efficient purification of expressed foreign protein.

Inactivation of components of the R. sphaeroides restriction/modification system enables greater stability of foreign DNA templates when they are introduced in the reaction mixture, eliminating concern that they encode sites for host restriction enzymes.

The R. sphaeroides genome encodes an Ion protease. Typically, this enzyme is inactivated in expression hosts of E. coli, (e.g., BL21). The strain also lacks the ompT protease. The Ion protease and others sharing similar inactivation status on E. coli strains are candidates for inactivation in strains of R. sphaeroides used as expression hosts, as are host proteins that copurify with target proteins during affinity chromatography. Gene deletions were performed by using a variation of published protocols to produce site-directed knockout mutations by homologous recombination. One published protocol is found at Pokkuluri et al, Biochemistry, Vol 41, pp 5998-6007 and incorporated herein by reference.

Briefly, segments that flank the gene to be deleted were amplified from the genome of Rhodobacter sphaeroides strain DD11. The amplified segments were cloned into suicide vector pSUP202 on either side of a gene encoding an antibiotic resistance marker. The suicide plasmid was introduced into the recipient host strain via conjugation. Plasmid pSUP202 is incapable of replication in Rhodobacter, thus its functions are lost unless they become integrated into the chromosome by hyomologous recombination. The presence of a dual crossover event that successfully deleted the candidate gene was confirmed by gain of antibiotic resistance and diagnostic PCR.

Reaction Mixture Modifications

To increase the versatility of a Rhodobacter-based membrane protein expression system, it is desirable to develop a means to label expressed proteins with other unnatural amino acids, amino acid analogs, or isotopically-labeled amino acids. In addition, while Rhodobacter is known to produce a variety of complex and redox cofactors, a general expression system would benefit from the ability to complement the native suite of cofactors with additional ones. Inasmuch as the cell-free system provides an open vessel-type feature, adding the desired label to the reaction mixture provides the means for labeling target proteins.

The determination of de novo x-ray protein structures involves the use of multiple- or single anomalous-wavelength dispersion (MAD/SAD) techniques. The incorporation of a selenium atom into the protein crystal is one way to provide an anomalous scatterer as a key to solving the crystal structure by these techniques. Selenium may be incorporated into a protein sequence by substitution of the amino acid analogue SeMet in the reaction mixture.

Membrane Solubilization/Detergent Selection Detail

Generally, the cell-free system eliminates the need for detergent optimization to produce membrane proteins in a natively-folded, functionally-active form. For functional or NMR studies, newly-synthesized proteins embedded in the ICMs often can be used without further processing.

Eliminating the need to solubilize precipitated membrane proteins expressed in a cell-free system increases the likelihood of maintaining the protein's native structure and function.

If extraction of the protein from the membranes is necessary, the inventor's knowledge about the actions of various detergents in purification of active membrane proteins from *Rhodobacter* ICMs can be utilized.

*Rhodobacter* ICM can be broken down with detergents that are considered to be fairly 'gentle' (e.g., Deriphat 160, dodecyl maltoside and octyl glucoside).

In one embodiment of the invented method, initial immobilized metal affinity chromatography(IMAC)-bound protein is washed with detergent-containing buffers with minimal or no imidazole until the monitored A280 nm falls below 100 mAU (0.1 OD). Detergent utilized in this wash step does not necessarily need to match that of the detergent used for solubilization, but often it does. Detergent exchange during washing is straightforward and quantitative as long as wash volumes exceed five column volumes. Extra buffer must be utilized when the critical micelle concentration of the new detergent is greater than that of the previous detergent. Further detergent details are found in Laible, P. D., Scott, H. N., Henry, L., and Hanson, D. K. (2004) Towards higher-throughput membrane protein production for structure genomics initiatives., *Journal of Structural and Functional Genomics* 5, 167-172, and incorporated herewith by reference.

By screening a large number of detergents against a small number of target proteins, one can optimize the first step of solubilization (dismantling the bilayer) to determine which types of detergents are best at integrating, penetrating, and ultimately destroying the lipid bilayer of the ICM. The same set of detergents work well for any membrane protein that is localized to the ICM and can be used in a generic approach. An embodiment of the invented method uses Deriphat 160 detergent (Cognis Care Chemicals, St. Fargeau Pthierry, France) when *Rhodobacter* membranes are utilized.

Culturing/Separation Protocol for Membrane Vesicles

Figure 4:
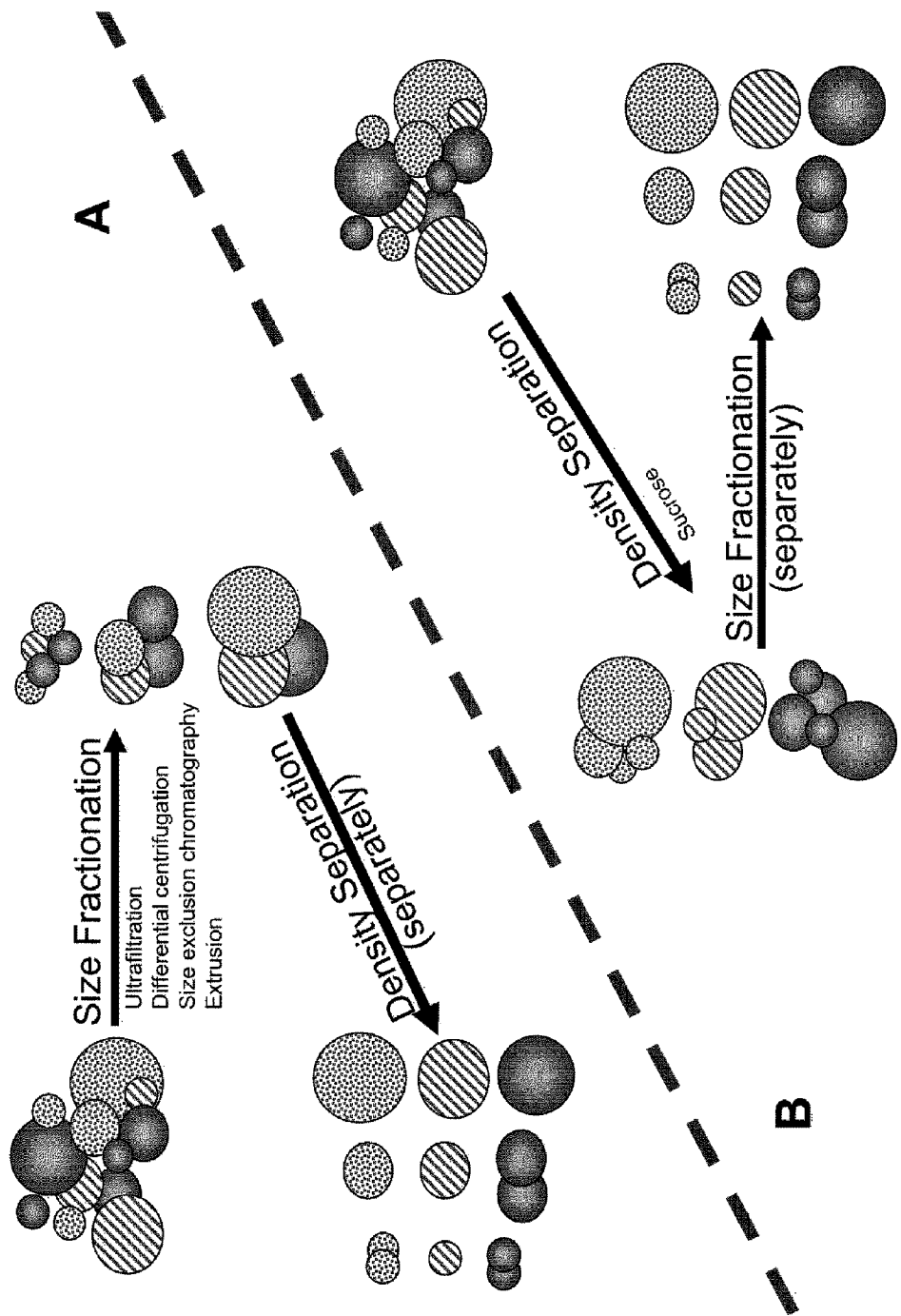
FIG. 4 is a schematic diagram of various strategies for separating intracytoplasmic membrane fractions, in accordance with features of the present invention.

The invention establishes culturing and separation protocols for production and isolation of membrane vesicles from engineered strains of *Rhodobacter* for use in the incorporation of nascent hydrophobic polypeptides. FIG. 4 provides detail in this regard. FIG. 4A shows how a conglomeration of membranes is first subjected to size fractionation, such as ultrafiltration, differential centrifugation, size exclusion chromatography or extrusion. Then the subjected membranes are subjected to density separation.

Alternatively, FIG. 4B depicts a membrane conglomeration first treated via density separation, via discontinuous sucrose gradient or similar means. Then the separated membranes are treated via size fractionation. A wide variety of host strains that differ in the composition of native protein found in their intracytoplasmic membranes is available.

Protocols for the preparation of inside-out membrane vesicles and for the production of spheroplasts are described below and also in the literature. When inside-out membrane veiscles are used, the cytoplasmic face of the ICM proteins is exposed and periplasmic proteins are captured in the interior of the vesicles. When spheroplasts are used, the peri-plasmic surfaces of ICM-bound proteins are exposed, while interior cellular components are inaccessible to reagents that remain outside the spheroplast.

Methods to produce membrane sheets that expose both membrane surfaces to the milieu are also described below and in the literature.

These membrane subpopulations have utility in functional studies, biochemical assays, and in the production of ordered arrays for structural analysis. They also serve as starting material in a subtractive strategy for the selection of affinity reagents to exposed periplasmic or cytoplasmic surfaces of the target membrane protein—the subtractive subset is obtained by producing ICM subpopulations from the corresponding engineered control strain of *R. sphaeroides* carrying an empty expression vector. Membrane fragments or vesicles harboring the expressed target membrane protein could be immobilized with a defined orientation via tags expressed on its exposed surfaces, facilitating sidedness in selection schemes or functional assays.

Figure 2:
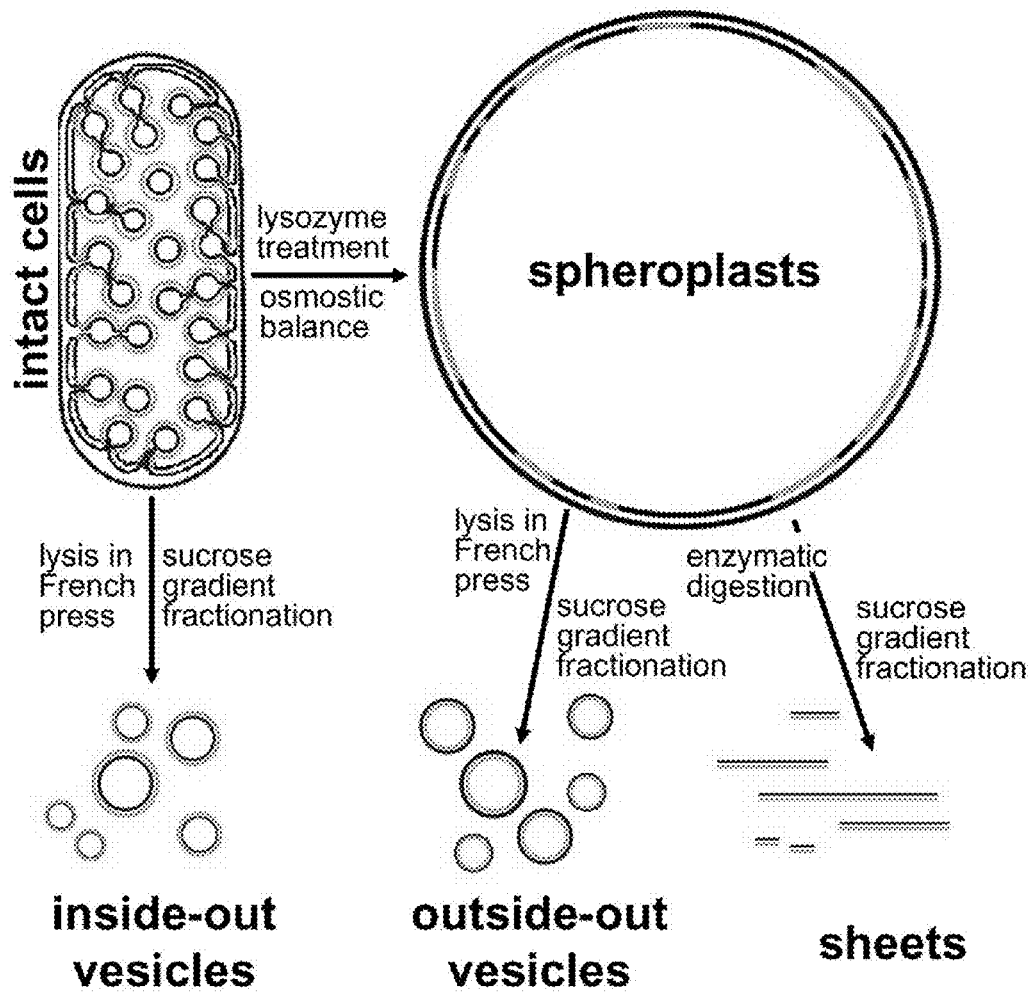
FIG. 2 is a schematic view of protocols to develop myriad vesicles and fragments from intracytoplasmic membranes, in accordance with features of the present invention.

*Rhodobacter* membrane subpopulations tested in the cell-free approachare depicted in FIG. 2. Protocols for producing each class of membrane subpopulation are well documented, as are methods for characterizing their protein complement and orientation/sidedness, i.e., their "purity". In each of these protocols, ICM-specific fractions can be isolated easily from other cellular components via density separation. Some fragments require preparation of spheroplasts as an intermediate in the isolation procedure.

In one embodiment, sedimented cells are resuspended in the above mentioned Tris buffer, additionally containing either 5 mM EDTA for chemotrophically grown cells, or 25 mM KCl and 10 mM $MgCl_2$ for photo-trophically grown cells. After homogenization of cells in a French pressure cell at 92 MPa, the homogenates were centrifuged at 33,000×g for 20 min. Subcellular fractions of chemotrophically grown cells were isolated by method A and of phototrophically grown cells with rate-zone sedimentation on sucrose density gradient by method B. Method A: the supernatant after the 33,000×g centrifugation (crude extract) was centrifuged for 60 min at 104,000×g, the pellet was washed (175,000×g for 40 min) and is designated as PI00. The supernatant was recentrifuged at 314,000×g for 90 min. The washed pellet (314,000×g for 90 min) is designated as P300. The remaining supernatant was concentrated 20-fold by ultrafiltration using a Diaflo PM10 filter (Amicon, Lexington, Mass. USA). This concentrate is designated in the following as the "soluble" fraction.

Method B: the crude extract was layered on top of a discontinuous sucrose gradient (3 ml of 2 M+2.5 ml of 1M+2 ml of 0.5 M sucrose) in the above Tris buffer for phototrophically grown cells and centrifuged at 200,000×g for 15 h. After the run the tube contents were fractionated into aliquots of 0.25 ml. Four main fractions were pooled: i) soluble fraction, ii) orange pigmented band, iii) intracytoplasmic membrane (ICM) and iv) the pelleted ribosomes. These, and other suitable protocols are disclosed in Dierstein, R., Schumacher, A., and Drews, G. (1981) On insertion of pigment-associated polypeptides during membrane biogenesis in *Rhodopseudomonas capsulata*. *Archives of Microbiology* 128, 376-383. Jungas, C., Ranck, J. L., Rigaud, J. L., Joliot, P., and Vermeglio, A. (1999) Supramolecular organization of the photosynthetic apparatus of *Rhodobacter sphaeroides*. *Embo J* 18, 534-42. Lommen, M. A., and Takemoto, J. (1978) Comparison, by freeze-fracture electron microscopy, of chromatophores, spheroplast-derived membrane vesicles, and whole cells of *Rhodopseudomonas sphaeroides*. *J Bacteriol* 136, 730-41. Reilly, P. A., and Niederman, R. A. (1986) Role of apparent membrane growth initiation sites during photosynthetic membrane development in synchronously dividing *Rhodopseudomonas sphaeroides*. *J Bacteriol* 167, 153-9. Takemoto, J., and Bachmann, R. C. (1979) Orientation of chromatophores and spheroplast-derived membrane vesicles of *Rhodopseudomonas sphaeroides*: analysis by localization of enzyme activities. *Arch Biochem Biophys* 195, 526-34. The aforementioned references are incorporated in their entirety by reference.

The three major classes of subpopulations include the following: Inside-out vesicles. These vesicles are obtained easily by mechanical disruption of *Rhodobacter* cells. Their outer surface is the cytoplasmic face of the intracytoplasmic membrane. On the interior surface of the particle is the periplasmic face of the membrane. The interior of the particle is a hydrophilic environment that encloses soluble components of the periplasmic space. This is a reducing environment and includes enzymes that assist with protein maturation (e.g., disulfide bond formation and heme maturation and attachment). The outside surface contains membrane-bound proteins that assist in the folding and insertion of membrane proteins.

Production of these membrane fractions is routine. In one protocol, spheroplast-derived vesicles are prepared from high-light or chemoheterotrophically-grown cells. For lysis, spheroplast preparations were diluted 10-fol with 10 mM Tris-HCl, pH 8.0 with stirring at room temperature. Brij 58 was then added to a final concentration of 0.02% (w/v) and the mixture was incubated for 30 min.

Alternatively, simultaneous formation and lysis of spheroplasts was performed in the same mixture. In this case, 25 ml of 16% (w/v) sucrose was used instead of 50% (w/v) sucrose and Brij 58 was included initially at a final concentration of 0.02% (w/v). Dilution was not required in this alternative lysis procedure. Lysis by either method yielded similar results.

To a lysed spheroplast preparation equivalent to 10 ml of cell suspension was added 2 ml of 0.1 M MgCl, and 1 to 5 mg of DNase I. The mixture was incubated for 30 min at 37° C. with gentle stirring. The crude suspension was centrifuged at 3000×g for 5 min and the pigmented supernatant fraction was recovered and centrifuged at 48,000×g for 30 min. The pellet was suspended in 10 mM Tris-HCl, pH 7.5 and homogenized with a Dounce homogenizer. The suspension was then layered onto 30 to 55% (w/v) linear sucrose gradients made up in the same buffer and centrifuged for about 10 h in a Beckman SW 41 rotor at 150,000×g. The pigmented materialsedimenting at approximately 38% (w/v) sucrose was recovered and washed by suspension in 10 mM Tris-HCl, pH 7.5 and centrifugation at 48,000 g for 30 min. All centrifugation and homogenization procedures were performed at 5° C.

Further details of vesicle production is found in Takemoto J and Bachmann R C (1979) "Orientation of chromatophores and spheroplast-derived membrane vesicles of *Rhodopseudomonas sphaeroides*: analysis by localization of enzyme activities." Arch Biochem Biophys 195: 526-534, and incorporated herein by reference. Suitable other protocols, aside from that disclosed herein, are generally found in the literature, including Lommen, M. A., and Takemoto, J. (1978) Comparison, by freeze-fracture electron microscopy, of chromatophores, spheroplast-derived membrane vesicles, and whole cells of *Rhodpseudomonas sphaeroides*. J Bacteriol 136, 730-41. Takemoto, J., and Bachmann, R. C. (1979) Orientation of chromatophores and spheroplast-derived membrane vesicles of *Rhodopseudomonas sphaeroides*: analysis by localization of enzyme activities. Arch Biochem Biophys 195, 526-34, the aforementioned papers incorporated herein by reference.

With the in vivo *Rhodobacter* expression system, foreign membrane proteins are targeted to the ICM and these inside-out vesicles are the starting material in protein purification procedures and are used in functional assays.

Outside-out vesicles. This type of sample is produced via generation of spheroplasts as a precursor. A suitable preparation of outside-out vesicles is found in the above-mentioned Takemoto reference, and includes the following steps. Cells are resuspended to OD 680=40 in buffer comprising 10 mM Tris, ph 7.8 and 100 mM NaCl. To every 10 mls of this resuspension is added Buffer 1 comprising 5.5 mls water. 5 mls 1 MTris, pH 8.0, 25 mls 40 percent sucrose (w/v), 2.5 mls lysozyme (10 mg/ml; fresh) and 2 mls 0.05 M EDTA.

This mixture is incubated for 30 minutes at 37 C. Then, 75 mls of 10 mM Tris, pH 8.0 and Brij-58 (0.03%) are added. This mixture was then incubated 30 minutes at room temperature.

DNase and 0.1 M MgCl2 was added, and the mixture again incubated for 30 minutes at 37 C. Debris was removed from the mixture at 3000×g over 5 minutes. The remaining supernatant was treated at 245,000×g for one hour to provide a pelletized fraction of membrane. The membrane pellet was then resuspended in Buffer 1 at 12 ml per gram. Alternatively, the supernatant was treated at 500,000×g for 2 hours, and resuspended in Buffer 1. A protocol for washing the outside-out membranes includes resuspending the pelletized membranes in 12 ml per gram, then repelletizing the membranes at 245,000 gram for one hour and finally resuspending in Buffer 1.

Treatment of *Rhodobacter* cells with lysozyme and EDTA in an osmotically-stabilized solution yields spheroplasts (FIG. 2). Upon disruption of cells by osmotic shock or mechanical means, outside-out vesicles of varied size can be produced per the protocols disclosed in the aforementioned papers incorporated by reference, namely Takemoto, J., and Bachmann, R. C. (1979) Orientation of chromatophores and spheroplast-derived membrane vesicles of *Rhodopseudomonas sphaeroides*: analysis by localization of enzyme activities. Arch Biochem Biophys 195, 526-34. The ones most enriched in lipids and proteins of the ICM can be isolated by density separation methods (see below). In this case, the membrane surfaces have the opposite orientation as the inside-out vesicles described above; soluble cytoplasmic components are trapped on the inside of these vesicles while soluble periplasmic components are released into the medium and removed when these vesicles are harvested by centrifugation.

Sheets. Either mechanical or enzymatic lysis methods diagrammed in FIG. 2 can also produce membrane sheets as a subpopulation. In brief, these membrane fragments are prepared according to the protocol used for preparation of outside-out vesicles when using a host strain known to form tubular ICMs. This fraction often takes the form of ordered two-dimensional arrays of protein and lipid and can be separated from the other vesicle types with density gradient centrifugation. In one suitable protocol, cells were supplemented with 500 ml of protease inhibitor cocktail per 25 ml of cells along with a few crystals of DNase I prior to passage through a French press thrice at 3000 psi. Whole cells and cell wall material were pelleted at 10 000×g for 10 min. The supernatant was placed onto a 15/40/50% w/w sucrose/membrane buffer density gradient and spun for 4 h at 100 000×g. The corresponding band was diluted 10-fold in membrane buffer and centrifuged for 4 h at 100 000 g. The pellet was resuspended overnight in 50 mM HEPES at pH 8 containing 0.03% a-dodecyl maltoside (DDM), gently homogenized and loaded onto a 30-50% w/w continuous sucrose gradient in 50 mM HEPES at pH 8 containing 0.03% DDM. Samples were centrifuged for 20 h at 200,000×g. Pigmented bands were harvested and frozen. Further details are found in Siebert C A, Qian P, Fotiadis D, Engel A, Hunter C N and Bullough P A (2004) Molecular architecture of photosynthetic membranes in *Rhodobacter sphaeroides*: the role of PufX. Embo J 23: 690-700, and incorporated herein by reference.

The proportion of sheets can be increased by manipulating the membrane protein complement of the host strain as described below. These fragments present both membrane surfaces to the surrounding medium.

The final step used in separation of membrane subpopulations is sucrose density gradient centrifugation. There are several distinct membrane fractions that can be separated effectively with this technique. In the event that cleaner membrane preparations are necessary, a two-step isolation procedure can be adopted that separates subpopulations by both size and density, as depicted in FIG. 4.

Treatment of either inside-out or outside-out vesicles with sub-critical micellar concentrations (CMC) of detergent (e.g., 0.03% LDAO) leaves the vesicles intact but permeabilizes them such that trapped soluble proteins can diffuse out. If this treatment is desired, the added detergent could be removed by collecting the membranes via ultracentrifugation following treatment and resuspension in a detergent-free buffer.

A factor affecting the nature of membrane samples (size, morphology, abundance, protein complement) that are produced is the identity of the host from which they were derived. The utility of membrane samples produced from the various hosts outlined supra have been examined, with ΔΔ1-derived extracts (FIG. 6) being superior to ATCC 17023. These experiments have determined the importance of vesicle morphology and protein content on the yield of incorporation of foreign membrane protein synthesized in vitro. Timing of the cell harvest may prove to be critical. The inventors hypothesize that there is a point in the auto induction cycle where the maximal amount of the preferred membrane fractions are produced. Also, photosynthetic growth modes versus chemo-heterotrophic growth modes may yield differences.

While the Rhodobacter-based cell-free reactions are discussed herein for illustrative purposes, ICM prepared from Rhodobacter and used in conjunction with commercial E. coli and wheat germ extracts are other options. The optimal amount of membranes to add is empirically determined by titrating to determine the levels that maximize yield of protein incorporation and minimizing inhibition of the synthesis reactions. Proteins localize to added ICMs when the ICMS represent about 0.5 to 10 percent of the reaction mixture.

While added membrane vesicles/fragments are considered "contaminants", the inventors found such surplus as providing services that trump this potential drawback. First, in addition to their low cost, the fragments also have a well-defined biochemical composition. So, the inventors know which detergents are efficient at dismantling them while still retaining protein function as the first step in purification. In functional assays (or in NMR experiments), vesicles incorporating newly synthesized (labeled) membrane proteins can bypass purification and can be used directly.

Second, preferably, the orientation of the membrane provides a protein surface for the binding of ligands and interactions with other proteins in functional assays. In addition, membrane fragments that differ in their "sidedness" aid in the selection of antibodies specific for periplasmic or cytoplasmic surfaces of integral membrane proteins. Finally, these cell-derived membrane subpopulations bring with them chaperones and membrane insertion factors that are likely to have a beneficial influence on the yield of natively-folded membrane protein produced in the cell-free system.

Template Detail

The efficacies of various templates have been compared. The input of target genes on smaller and relatively easy to produce PCR products versus on plasmids eliminates a cloning step. Also compared are message levels from endogenous promoters versus those from a heterologous promoter, e.g., T7 from bacteriophage. Design features that stabilize templates over the duration of the transcription and translation reactions are provided. The inventors have found that multiple types of templates are compatible in cell-free protein synthesis reactions involving Rhodobacter extracts. Further, DNA or RNA templates which encode single target protein or multiple target proteins, are suitable. The multiple genes can reside on a single PCR amplicon or on multiple PCR amplicons. Alternatively, or in addition, the multiple genes reside on a single plasmid. In an embodiment of the invented system, multiple plasmids are used for the production of multiple proteins.

To increase the throughput of the system, it was determined that PCR fragments are viable alternatives to the use of plasmids as DNA templates for transcription. At a minimum, these amplicons contain promoter and ribosome binding sequences, sequences encoding tags for affinity purification, and downstream terminators; other sequences that protect against their digestion by exo- and endonucleases could be incorporated as well.

Two promoters were tested. Since the inventors have a library of hundreds of plasmid constructs that carry the puf or puc promoter of Rhodobacter, testing can be done in a Rhodobacter extract where translation is inhibited by the addition of chloramphenicol. As an alternative, the inventors can generate PCR amplicons that carry the T7 promoter sequence and generate mRNA in vitro by transcribing them with T7 polymerase that has been added to the Rhodobacter extract, again, where translation has been inhibited. The levels of mRNA can be quantified using RTPCR.

Figure 9:
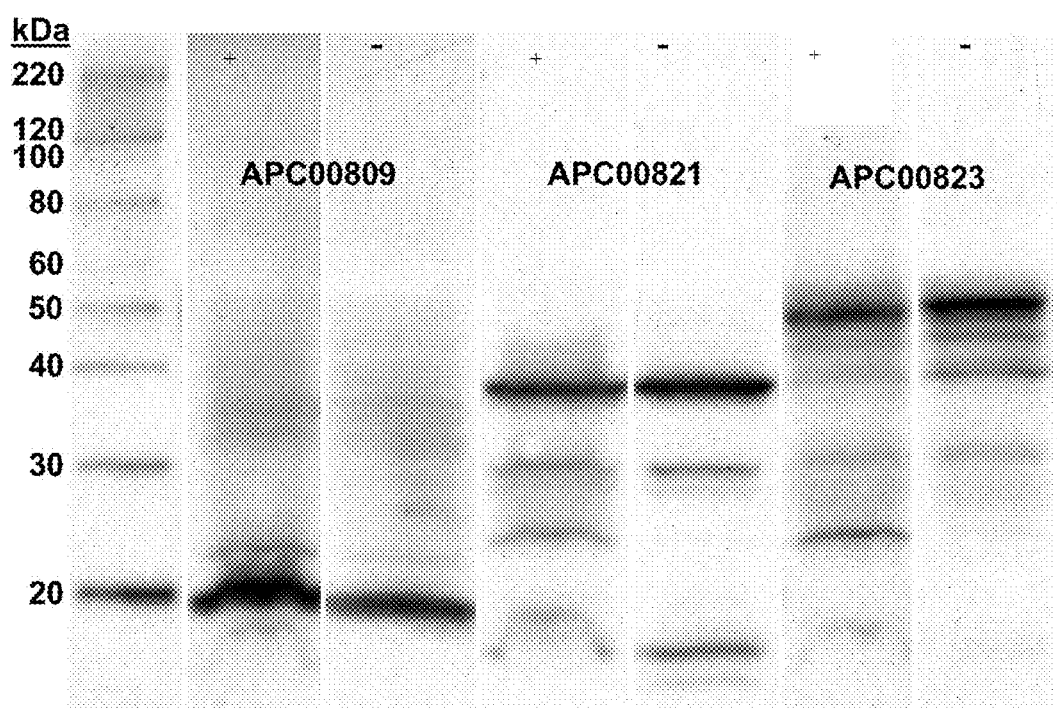
FIG. 9 is an immunoblot showing yield of target proteins in the presence and absence of intracytoplasmic membrane vesicles, in accordance with features of the present invention.

FIG. 9 is an immunoblot showing yield of target proteins in the presence and absence of intracytoplasmic membrane vesicles Immunoblot (anti-polyhistidine) analysis of the yield of target membrane proteins from cell-free reactions performed in the presence (+) or absence (−) of added Rhodobacter ICMs. Target proteins range from 20-52 kDa. Similar amounts of target protein are produced in each reaction. In the first case, APC00809, more protein is produced in the presence of added membranes. In the third case, APC00823, slightly less target protein is produced in the presence of ICM. In the second case, APC00821, about an equal amount of target protein is produced in the presence of ICM. In all cases, significant amounts of target protein are produced. Thus, the added membranes are not overly inhibitory and actually increase yield in some cases.

Translations occurred and correlations were seen between mRNA levels and expression of selected "reporter" proteins such as soluble GFP and membrane proteins that are known to express well from the puf promoter in the in vivo expression system (e.g., APC00809, APC00821, APC00823; see FIG. 9).

Protein yield can be determined spectroscopically (for GFP) or by SDS-PAGE; (for membrane proteins), and mRNA levels can be quantified by RT-PCR. This information provides a means for understanding how to maximize the relationship between proteins synthesized and proteins partitioned into membranes in the coupled transcription/translation system. For example, it would not be desirable to produce so much protein that the majority of it precipitates before it is incorporated into the added membranes.

In an embodiment of the invention, either endogenous or exogenous RNA polymerases, or both types simultaneously, can be used in the initial reaction mixture (i.e., the transcription/translation-competent cellular extract) to facilitate transcription. The activities of endogenous RNases can be curtailed by addition of commercially-available inhibitors. Where DNA stability is a major limitation, host strains can be further engineered to delete nucleases (e.g., RshI). Genome engineering is accomplished by marker recycling techniques, such as those systems of antibiotic marker recycling in Gram negative bacteria that is based on cre-lox site-specific recombination methodology. An exemplary protocol of the methodolgy is disclosed in Marx, C. J., and Lidstrom, M. E. (2002) Broad-host-range cre-lox system for antibiotic marker recycling in gram-negative bacteria. *Biotechniques* 33, 1062-7, and incorporated herein by reference. This strategy is assisted by knowledge of the complete genome sequence of *R. sphaeroides* which is publicly available (See Internet website "The *Rhodobacter sphaeroides* genome project" hosted by the University of Texas—Houston, Health Science Center, Department of Microbiology & Molecular Genetics). Where *Rhodobacter*'s preference for GC-rich codons proves to be a problem, genes for relatively rare tRNAs are supplied on a plasmid; alternatively, these tRNAs could be synthesized in vivo in host strains carrying such a plasmid and therefore represented in extracts prepared from those host strains.

Uncoupling of Transcription and Translation Reactions

Reaction yields for the translation and translocation of polypeptides can be optimized from carefully controlled levels of message. Defined amounts of purified mRNA (derived from reactions containing T7 polymerase and T7-promoted genes encoding reporter membrane proteins, or other membrane proteins that are expressed efficiently in the in vivo *Rhodobacter* expression system) are added to extracts and reagents listed in Table 1. Degradation paths can be minimized with nuclease inhibitors and/or production of extracts from engineered strains where nucleases have been knocked out.

Protein yields are quantified using stained SDS-PAGE gels and immunoblots. Message levels can be titrated, initially in the absence of membrane additions, to determine the point at which the amount of protein synthesized plateaus. The dependence of that plateau on the availability of rare tRNAs can be determined by testing extracts derived from strains characterized by the presence or absence of a "magic" plasmid supplying genes for these tRNAs (see Culturing/Separation Detail, supra). Translation reactions at several time points can be sampled to determine the lifetime of the extract in protein synthesis in experiments where reagents are not replenished.

Large Scale
Synthesis Detail

Many variants of reactors for large-scale synthesis of soluble proteins in cell-free systems are available commercially as kits from, e.g., TNT Quick Coupled Transcription/Translation Systems from Promega, Expressway Cell-free Expression Systems from Invitrogen, and Rapid Translation System Kits from 5 PRIMEGmbH. Most feature some type of permeable membrane through which reaction products and byproducts can be removed while fresh synthesis reagents can be introduced. These membranes are designed to retain the high molecular weight components of the transcription/translation apparatus while allowing synthesized protein to pass through.

In the event that membranes prove inhibitory and must be removed and replenished along with other reagents, this can be accomplished by periodic differential ultracentrifugation of the reaction mixture or methods of ultrafiltration that take advantage of the size of the membrane fragments and/or the tagged proteins that reside within them.

Semi-Automated Purification Detail

Purifications of the target proteins from cell-free reactions are simpler than purification that begins from whole cells as the overall protein load is smaller and the amount of co-purifying, histidine-rich endogenous *Rhodobacter* proteins is greatly reduced.

Example

The following is an exemplary cell-free expression system based upon extracts of *Rhodobacter* cells used in in vitro synthesis of selected membrane proteins. Transcription/translation-competent extracts are prepared according to methods described below. Briefly, cells grown semi-aerobically were harvested, resuspended in a buffer solution [10 mM Tris-acetate, pH 8.2, 60 mM potassium acetate, 15 mM magnesium acetate, 1 mM dithiothreitol], and lysed by two passages through a French pressure cell at 12,000 psi. The lysate was then centrifuged for 30 minutes at 30,000×g. Details of such preparation are also found in Chory, J., and Kaplan, S. (1982) The in vitro transcription-translation of DNA and RNA templates by extracts of *Rhodopseudomonas sphaeroides*. Optimization and comparison of template specificity with *Escherichia coli* extracts and in vivo synthesis. J Biol Chem 257, 15110-21. Troschel, D., and Muller, M. (1990) Development of a cell-free system to study the membrane assembly of photosynthetic proteins of *Rhodobacter capsulatus*. J Cell Biol 111, 87-94.

Endogenous mRNA was translated by incubation of the supernatant ("S30") for 1 hour at 32° C. in a mixture consisting of 0.87 M Tris-acetate, pH 8.2, 23 mM magnesium acetate, 8.7 mM dithiothreitol, 7.7 mM ATP, 0.087 mM of each of the 20 amino acids, 26 mg/ml phosphoenolpyruvate, and 25 μg/ml pyruvate kinase. Following dialysis against the above buffer, the S30 mixture was subjected to centrifugation at 135,000×g for 15 minutes to prepare a membrane-free extract ["S135"] that is transcription/translation competent. The inventors' experiments have shown that, unlike the situation in *E. coli*, an S135 extract derived from *Rhodobacter* is not membrane-free.

Small aliquots of the S135 extract were frozen at −80° C. In typical reactions, transcription and translation were initiated in this extract (40 μl in 100 μl reaction mixture) by the addition DNA template (5 μg) and the reagents outlined in Table 1, below.

TABLE 1

Cell-free reaction reagents

| Component | [final (mM)] |
|---|---|
| Tris-acetate, pH 8.2 | 40 |
| Potassium acetate | 34 |
| Ammonium acetate | 27 |
| Calcium acetate | 5 |
| Magnesium acetate | 5 |
| Phosphoenolpyruvate | 40 |
| Dithiothreitol | 1.4 |
| ATP | 2.2 |
| UTP, CTP, GTP | 0.54 |
| Folinic acid | 0.052 |
| Pyridoxine | 0.16 |
| NADP | 0.035 |
| FAD | 0.032 |
| p-aminobenzoic acid | 0.08 |
| Amino acids (mix of 20) | 0.22 |

Protease inhibitors, RNase inhibitor, and aliquots of *Rhodobacter* ICMs (typically 10 μl, but the optimum amount could range from 2-30 μl) were added to some reactions (see below). Reactions (100 μL) proceeded for 30 min at 32° C. Aliquots of the reaction mixture—total, or fractions separated by low-speed and/or high-speed centrifugation—were then separated by SDS-PAGE and the target protein was identified on immunoblots of those gels that were probed with a monoclonal antipolyhistidine primary antibody followed by a horseradish peroxidase-coupled secondary antibody.

It should be appreciated that the components of the reaction mixture are provided either in batch or continuously. Continuously replenishing the components, via dialysis or similar means, assures continual operation of the method, and therefore maximizes production and sequestration of target proteins. As long as the extract remains active, the continuous method replaces "full membranes" (i.e. membranes containing target protein) via centrifugation or other separation means, with new membrane feedstock.

These experiments demonstrate that the *Rhodobacter* extracts are capable of coupled transcription/translation reactions, that added intracytoplasmic membranes do not inhibit the synthesis reactions, and that the newly-synthesized membrane proteins can associate with the added membranes. The data from these preliminary experiments are described in detail below.

Membrane proteins selected for initial testing of the cell-free system were members of the *E. coli* membrane proteome, spanned a range of molecular weights, number of transmembrane passes, and isoelectric points, and were known to be expressed to high levels (>10 mg/L cell culture) in the cell-based system.

Figure 6:
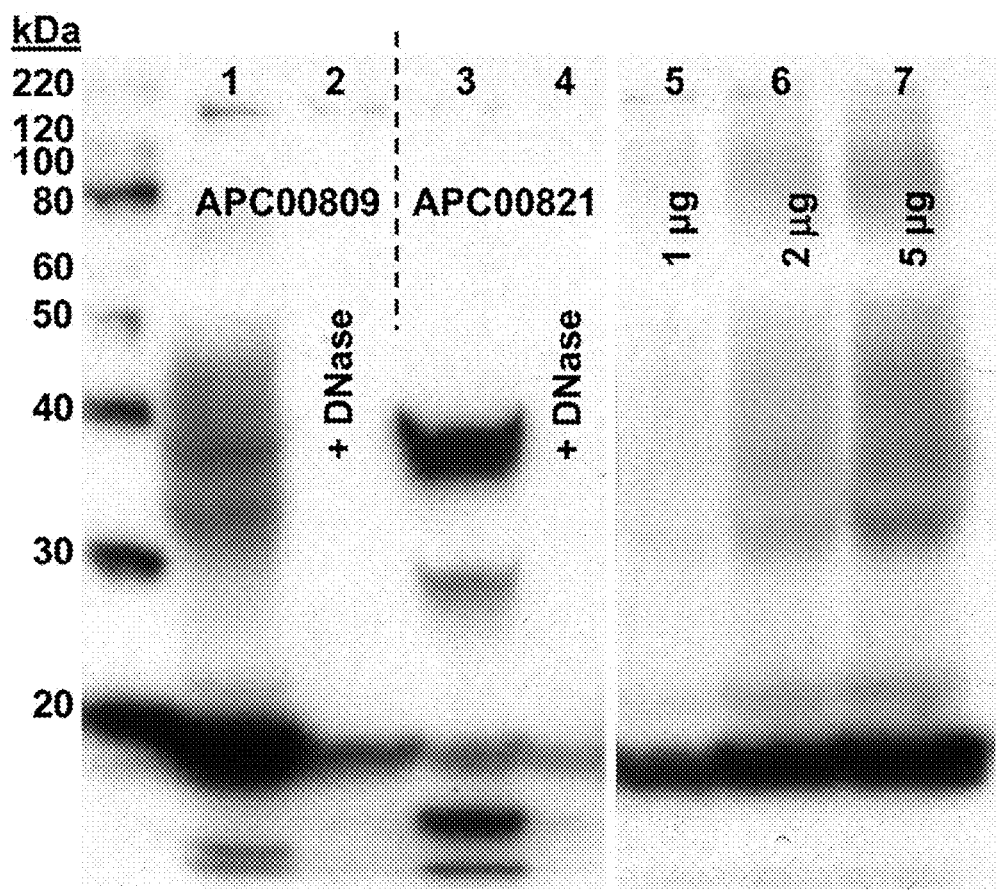
FIG. 6 shows DNA-dependent synthesis of two *E. coli* membrane proteins, in accordance with features of the present invention.

FIG. 6 depicts immunoblots (anti-polyhistidine) of cell-free reactions driven by *Rhodobacter* extracts. The reaction depends on the presence of DNA and its concentration. Small 22 kDa residual signals present in the DNase-treated samples have an apparent molecular weight that is the same as APC00809 (22 kDa). This protein is a component of the extract as the same band is also detected by the antibody in lanes for APC00821 (MW=40 kDa).

FIG. 6 shows DNA-dependent synthesis of two *E. coli* membrane proteins, APC00809 and APC00821. In each of these cell-free reactions, protein synthesis was primed by plasmid DNA-pRKPLHT1 derivatives carrying the gene of interest. In lanes 1 and 3, proteins of the expected sizes (APC00809=22 kDa; APC00821=40 kDa) are identified by the anti-polyhistidine antibody. In lanes 2 and 4, the template DNAs were treated with DNase prior to their addition to the reaction mixture, and the expected signals for the two proteins are absent. Lanes 5-7 demonstrate the direct relationships between the amount of protein synthesized (APC00809) upon the quantity of plasmid DNA that was added to the reaction. In this experiment, the template plasmids were prepared from *Rhodobacter* host strain. In contrast, the template plasmids prepared in *E. coli* failed to direct synthesis of proteins in S135 extract. These results suggested endogenous nuclease activities in the extract that recognized PCR products and *E. coli*-derived plasmid DNA as foreign.

The inventors' found that the addition of intracytoplasmic membrane vesicles from *Rhodobacter* aids in sequestering nascent membrane proteins when they are present during the course of the cell-free synthesis reaction. As a first step, the inventors tested whether the addition of ICMs would inhibit the reaction. The results of this experiment are presented in FIG. 9. Three target membrane proteins of different sizes were selected.

Plasmid DNA carrying the target genes were used to prime transcription and translation reactions as described above. Duplicate reactions were run, and *Rhodobacter* ICMs were added to 10% of the reaction volume to one set [10 μl of sucrose density gradient-purified membrane fragments, OD600=12.5].

The yield of target membrane protein that was synthesized in each of these reactions was then analyzed by SDS-PAGE and immunoblotting. The data show that similar amounts of protein were produced in all reactions.

Experimental results show that synthesized membrane proteins associate with membranes. Since expression in the presence of added ICMs was successful, centrifugal fractionation of the cell-free synthesis reaction following its completion was employed to localize and quantify the amount of target membrane protein that was associated with (i) the fraction that sediments with low-speed centrifugation ('debris'), (ii) the fraction that sediments only after ultracentrifugation (membranes), and (iii) the soluble fraction.

When using *Rhodobacter* extracts, a significant amount of the target protein is associated with the pellet obtained thereafter using ultracentrifugation (250,000×g, 20 min), representing the membrane pellet. Some of the target protein remains in the soluble fraction following that spin.

Figure 3:
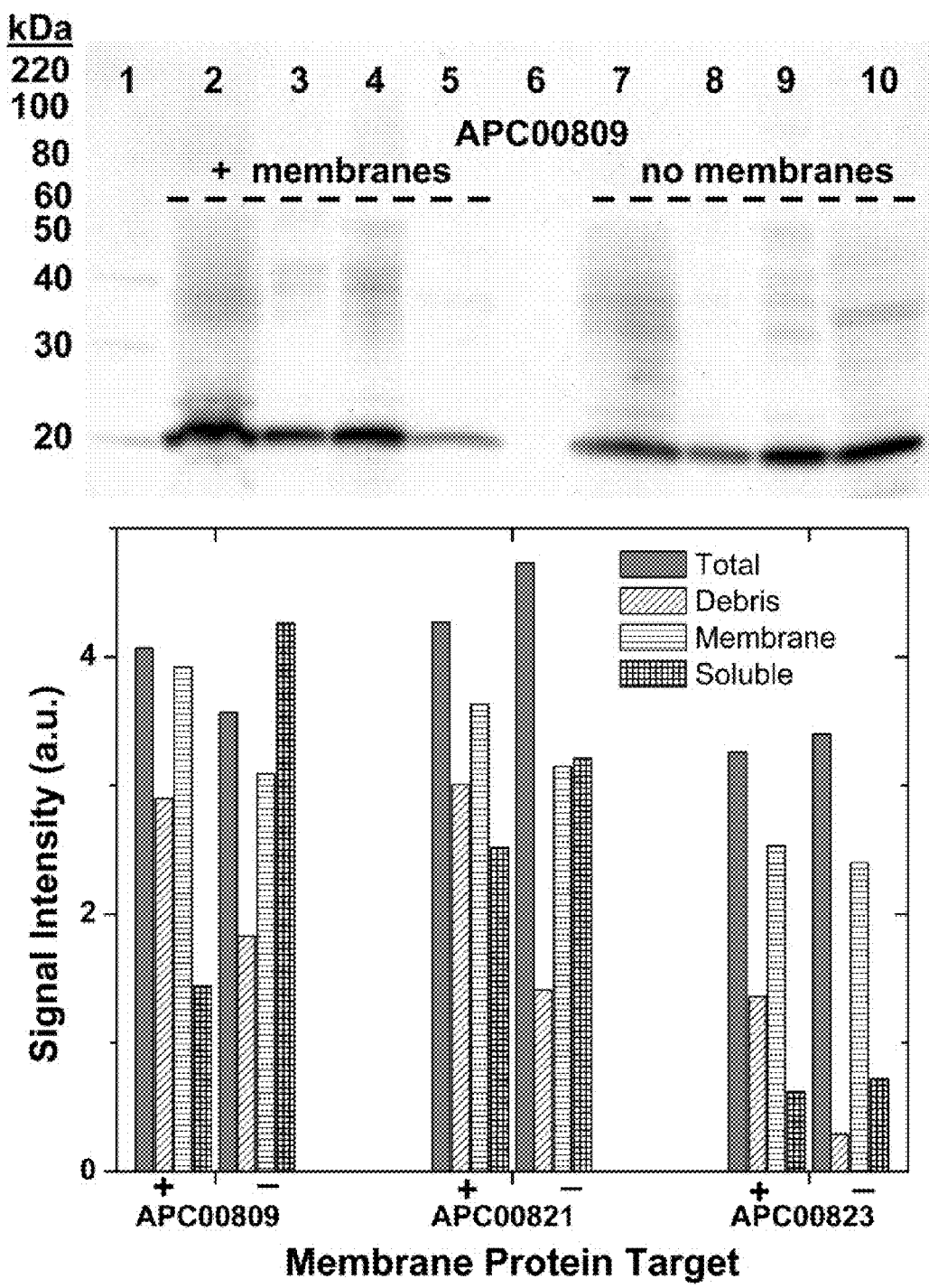
FIG. 3 is a graph depicting the efficiency of target membrane protein association/sequestration with intracytoplasmic membranes, in accordance with features of the present invention.

FIG. 3 is a graph depicting the efficiency of target membrane protein association/sequestration with intracytoplasmic membranes. In reaction fractionation experiments, target membrane protein associates readily with endogenous membranes from *Rhodobacter* extracts (top; right) and with membranes added during the reaction (top; left). Signals from immunoblots (anti-His; top) of total (lanes 2 and 7), debris (lanes 3 and 8), membrane (lanes 4 and 9) and soluble (lanes 5 and 10) fractions demonstrate, shown here for APC00809, the large fraction of that protein that is incorporated into membranes that pellet only after ultracentrifugation. Added membranes (top; left) enhance the relative proportion of the total protein associated (ionically, covalently, via hydrogen bonding or other measures) with the membrane. The added membranes decrease the relative proportion of the total protein that is associated with the soluble fraction. This large signal from membranes is a common result now observed with a range of target proteins (bottom).

The top panel of FIG. 3 shows that the addition of ICMs to the cell-free synthesis reaction enhances the amount of synthesized membrane protein that is associated with the membrane fractions and reduces the amount of it present in the soluble fraction. The experiment was extended to the three proteins shown in the bottom panel of FIG. 3. In all cases, the dominant signal from the fractionation efforts is that of the membrane fraction. Initial experiments have been performed to determine whether adding purified ICMs from host strains lacking some complement of native ICM proteins (ΔΔ11) could increase the amount of target protein that is found in the membrane pellet following fractionation of the cell-free synthesis reaction.

Figure 7:
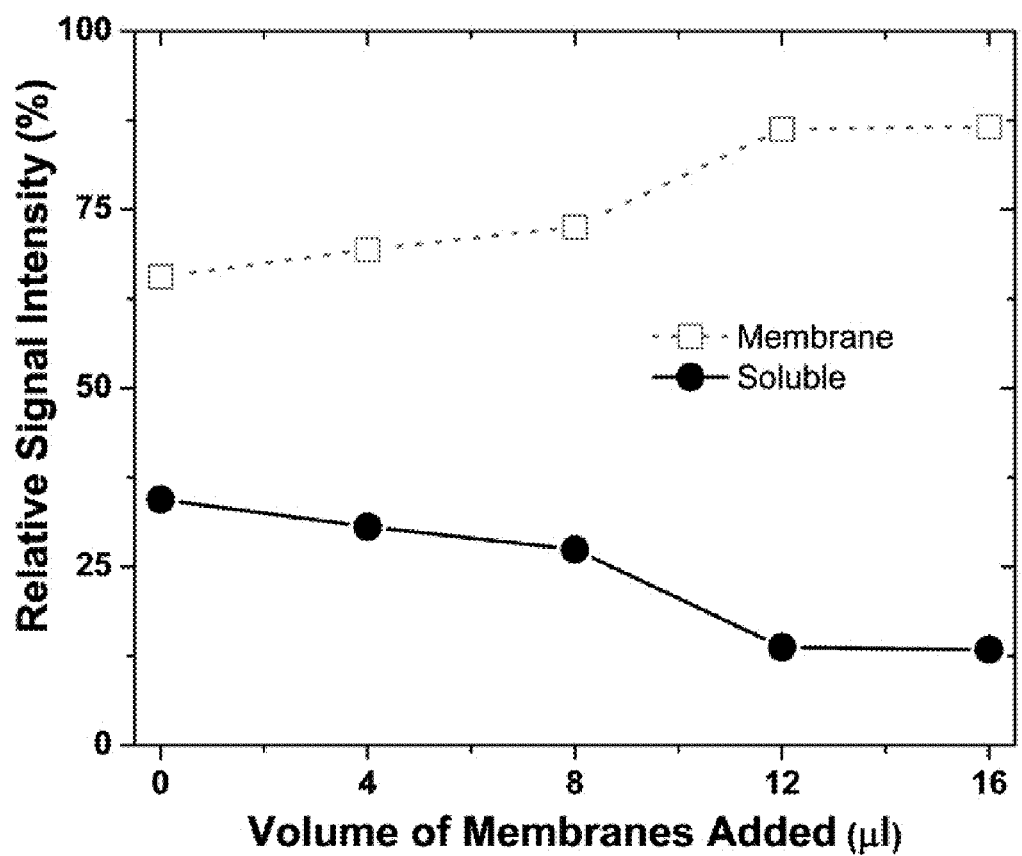
FIG. 7 is a graph showing the influence of intracytoplasmic membranes on the partitioning of target proteins into the soluble or membrane fractions of the reaction mixture, in accordance with features of the present invention.

Increasing amounts of gradient-purified ICMs (OD600=12.5) were added to four different cell-free reactions primed by plasmid DNA encoding membrane protein APC00809. The results are shown in FIG. 7. The amount of target membrane protein that is associated with the membrane fraction increases with the addition of ICMs and appears to plateau at higher membrane levels, but not before capturing more than 85 percent of the target protein produced in the reaction.

FIG. 7 is a graph showing the influence of intracytoplasmic membranes on the partitioning of target proteins into the soluble or membrane fractions of the reaction mixture. The partitioning of target proteins into soluble (closed circles) and membrane (open squares) fractions is influenced by the addition of membranes to the in vitro reaction. Here, target membrane protein APC00809 is found initially in a ratio of 2:1 in the membrane fraction with no membrane additions (relying solely on the endogenous membranes present in the S135 extract). The ratio increases to 7:1 with addition of 12-16 μl of an ICM preparation (OD600=12.5). The total yield of synthesized target membrane protein decreases only slightly in the presence of these membranes. Relative partitioning is shown.

Figure 8:
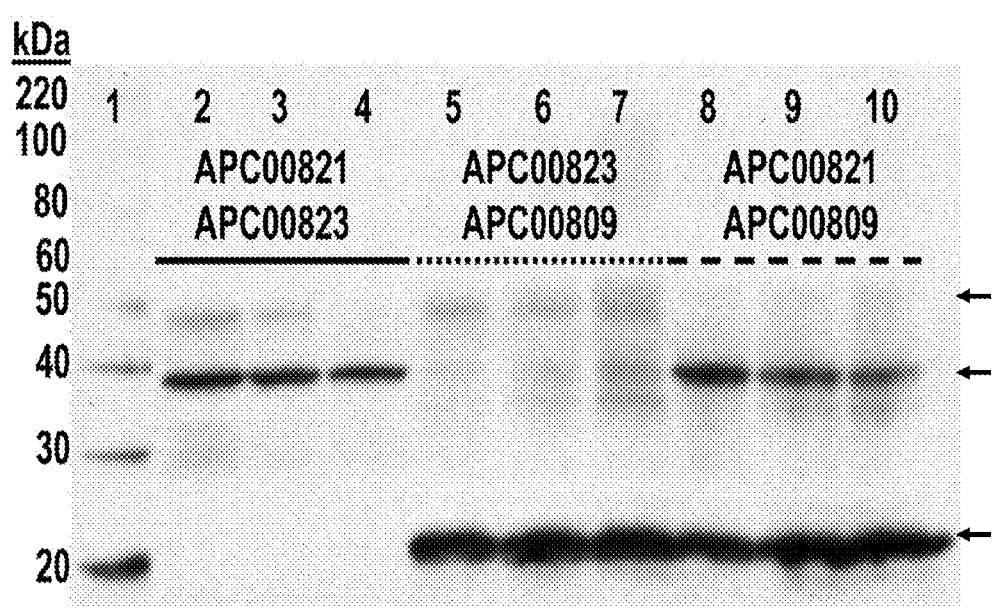
FIG. 8 is an immunoblot showing simultaneous synthesis and ICM localization of membrane proteins from two different DNA templates, in accordance with features of the in vitro method of the present invention.

The inventors have found that the *Rhodobacter* cell-free extracts are capable of synthesizing target membrane proteins from two different template DNAs that were added to the reaction. FIG. 8 displays immunoblots (anti-polyhistidine) of membrane fractions showing co-synthesis of two target membrane proteins in cell-free reactions. Each reaction was primed by two separate plasmids, each encoding one of the target membrane proteins (arrows). For each pair of target proteins, the weight ratios for the templates of the large protein:small protein ranged from 2:1 to 1:2.

FIG. 8 shows three weight ratios: 2:1, 1:1, and 1:2 (left, center, and right, respectively, for each set). Typical cell-free reactions containing 10 μl purified *Rhodobacter* ICMs were primed to synthesize two different membrane proteins. The reaction shows that the relative amounts of the synthesized proteins are controlled by the ratios of the two DNA templates added to the reaction. Exemplary routes for accomplishing this include the following strategies:

1) clone the requisite number of genes into the same expression plasmid behind the same promoter
2) supply the reaction with multiple plasmids, each of which drives the expression of a single gene that is required for making the complex
3) accomplish either of the above with PCR product(s)

In cases 2 and 3, putting the plasmids or PCR products into the reaction at the same time would result in simultaneous synthesis of subunits of the complex. Putting the plasmids or PCR products into the reaction at different times would facilitate serial synthesis, if one could envision cases where that would be most optimal. If the stoichiometries of the protein subunits in the complex are not 1:1, then cases 2 and 3 allow for adjustment of the ratios of the template supplied to the reaction.

The absolute amounts of the proteins synthesized and localized to the membrane fraction do not necessarily scale in this manner, due no doubt to the inequity in molar concentration caused by the difference in size of both the templates and the proteins that they encode. These data can also speak to the relative stabilities of their respective mRNAs and the ability of the synthesized polypeptides to be inserted into *Rhodobacter* membranes. The important result of this experiment is that it demonstrates the capability of the *Rhodobacter*-based cell-free system for co-expressing multiple subunits of a hetero-oligomeric membrane protein complex.

It is to be understood that the above description is intended to be illustrative, and not restrictive. For example, the above-described embodiments (and/or aspects thereof) may be used in combination with each other. In addition many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

```
Plasmid pRK404 Sequence
                                                                (SEQ. ID. 1)
     1gaattcaccc ccgaacacga gcacggcacc cgcgaccact atgccaagaa tgcccaaggt 61aaaaattgcc ggccccgcca tgaagtccgt gaatgccccg acggccgaag tgaagggcag 121gccgccaccc aggccgccgc cctcactgcc cggcacctgg tcgctgaatg tcgatgccag 181cacctgcggc acgtcaatgc ttccgggcgt cgcgctcggg ctgatcgccc atcccgttac 241tgccccgatc ccggcaatgg caaggactgc cagcgctgcc atttttgggg tgaggccgtt 301cgcggccgag gggcgcagcc cctgggggga tgggaggccc gcgttagcgg gccgggaggg 361ttcgagaagg gggggcaccc cccttcggcg tgcgcggtca cgcgcacagg gcgcagccct 421ggttaaaaac aaggtttata aatattggtt taaaagcagg ttaaaagaca ggttagcggt 481ggccgaaaaa cgggcggaaa cccttgcaaa tgctggattt tctgcctgtg gacagcccct 541caaatgtcaa taggtgcgcc cctcatctgt cagcactctg cccctcaagt gtcaaggatc 601gcgcccctca tctgtcagta gtcgcgcccc tcaagtgtca ataccgcagg gcacttatcc 661ccaggcttgt ccacatcatc tgtgggaaac tcgcgtaaaa tcaggcgttt tcgccgattt 721gcgaggctgg ccagctccac gtcgccggcc gaaatcgagc ctgcccctca tctgtcaacg 781ccgcgccggg tgagtcggcc cctcaagtgt caacgtccgc ccctcatctg tcagtgaggg 841ccaagttttc cgcgaggtat ccacaacgcc ggcggccgcg gtgtctcgca cacggcttcg 901acggcgtttc tggcgcgttt gcagggccat agacgccgc  cagcccagcg gcgagggcaa 961ccagcccggt gagcgtcgga aaggcgctct tccgcttcct cgctcactga ctcgctgcgc
```

-continued

```
1021 tcggtcgttc ggctgcggcg agcggtatca gctcactcaa aggcggtaat acggttatcc
1081 acagaatcag gggataacgc aggaaagaac atgtgagcaa aaggccagca aaaggccagg
1141 aaccgtaaaa aggccgcgtt gctggcgttt tccataggc tccgccccc tgacgagcat
1201 cacaaaaatc gacgctcaag tcagaggtgg cgaaacccga caggactata agataccag
1261 gcgtttcccc ctggaagctc cctcgtgcgc tctcctgttc cgaccctgcc gcttaccgga
1321 tacctgtccg cctttctccc ttcgggaagc gtggcgccat cgccattca ggctgcgcaa
1381 ctgttgggaa gggcgatcgg tgcgggcctc ttcgctatta cgccagctgg cgaaagggg
1441 atgtgctgca aggcgattaa gttgggtaac gccagggttt tcccagtcac gacgttgtaa
1501 aacgacggcc agtgaattcc cggggatccg tcgacctgca gccaagcttg gcgtaatcat
1561 ggtcatagct gtttcctgtg tgaaattgtt atccgctcac aattccacac aacatacgag
1621 ccggaagcat aaagtgtaaa gcctggggtg cctaatgagt gagctaactc acattaattg
1681 cgttgcgctc actgcccgct ttccagtcgg gaaacctgtc gtgccagctg cattaatgaa
1741 tcggccaacg cgcggggaga ggcggtttgc gtattgggcg ctcggtcttg ccttgctcgt
1801 cggtgatgta cttcaccagc tccgcgaagt cgctcttctt gatggagcgc atggggacgt
1861 gcttggcaat cacgcgcacc ccccggccgt tttagcggct aaaaaagtca tggctctgcc
1921 ctcgggcgga ccacgcccat catgaccttg ccaagctcgt cctgcttctc ttcgatcttc
1981 gccagcaggg cgaggatcgt ggcatcaccg aaccgcgccg tgcgcgggtc gtcggtgagc
2041 cagagtttca gcaggccgcc caggcggccc aggtcgccat tgatgcgggc cagctcgcgg
2101 acgtgctcat agtccacgac gcccgtgatt ttgtagccct ggccgacggc cagcaggtag
2161 gccgacaggc tcatgccggc cgccgccgcc ttttcctcaa tcgctcttcg ttcgtctgga
2221 aggcagtaca ccttgatagg tgggctgccc ttcctggttg gcttggtttc atcagccatc
2281 cgcttgccct catctgttac gccggcggta gccggccagc ctcgcagagc aggattcccg
2341 ttgagcaccg ccaggtgcga ataagggaca gtgaagaagg aacacccgct cgcgggtggg
2401 cctacttcac ctatcctgcc cggctgacgc cgttggatac accaaggaaa gtctacacga
2461 acccttggc aaaatcctgt atatcgtgcg aaaaaggatg gatataccga aaaatcgct
2521 ataatgaccc cgaagcaggg ttatgcagcg gaaaagcgcc acgcttcccg aagggagaaa
2581 ggcggacagg tatccggtaa gcggcagggt cggaacagga gagcgcacga gggagcttcc
2641 agggggaaac gcctggtatc tttatagtcc tgtcgggttt cgccacctct gacttgagcg
2701 tcgattttg tgatgctcgt caggggggcg agcctatgg aaaaacgcca gcaacgcggc
2761 cttttacgg ttcctggcct tttgctggcc ttttgctcac atgttctttc ctgcgttatc
2821 ccctgattct gtggataacc gtattaccgc ctttgagtga gctgataccg ctcgccgcag
2881 ccgaacgacc gagcgcagcg agtcagtgag cgaggaagcg gaagagcgcc agaaggccgc
2941 cagagaggcc gagcgcggcc gtgaggcttg acgctaggg cagggcatga aaagcccgt
3001 agcgggctgc tacgggcgtc tgacgcggtg aaaggggga ggggatgttg tctacatggc
3061 tctgctgtag tgagtgggtt gcgctccggc agcggtcctg atcaatcgtc acccttctc
3121 ggtccttcaa cgttcctgac aacgagcctc cttttcgcca atccatcgac aatcaccgcg
3181 agtccctgct cgaacgctgc gtccggaccg gcttcgtcga aggcgtctat cgcggcccgc
3241 aacagcggcg agagcggagc ctgttcaacg gtgccgccgc gctcgccggc atcgctgtcg
3301 ccggcctgct cctcaagcac ggccccaaca gtgaagtagc tgattgtcat cagcgcattg
3361 acggcgtccc cggccgaaaa acccgcctcg cagaggaagc gaagctgcgc gtcggccgtt
```

-continued

```
3421 tccatctgcg gtgcgcccgg tcgcgtgccg gcatggatgc gcgcgccatc gcggtaggcg
3481 agcagcgcct gcctgaagct gcgggcattc ccgatcagaa atgagcgcca gtcgtcgtcg
3541 gctctcggca ccgaatgcgt atgattctcc gccagcatgg cttcggccag tgcgtcgagc
3601 agcgcccgct tgttcctgaa gtgccagtaa agcgccggct gctgaacccc caaccgttcc
3661 gccagtttgc gtgtcgtcag accgtctacg ccgacctcgt tcaacaggtc cagggcggca
3721 cggatcactg tattcggctg caactttgtc atgcttgaca cttatcact gataaacata
3781 atatgtccac caacttatca gtgataaaga atccgcgcgt tcaatcggac cagcggaggc
3841 tggtccggag gccagacatg aaacccaaca taccctgat cgtaattctg agcactgtcg
3901 cgctcgacgc tgtcggcatc ggcctgatta tgccggtgct gccgggcctc ctgcgcgatc
3961 tggttcactc gaacgacgtc accgcccact atggcattct gctggcgctg tatgcgttgg
4021 tgcaatttgc ctgcgcacct gtgctgggcg cgctgtcgga tcgtttcggg cggcggccaa
4081 tcttgctcgt ctcgctggcc ggcgccactg tcgactacgc catcatggcg acagcgcctt
4141 tcctttgggt tctctatatc gggcggatcg tggccgcat caccggggcg actgggcgg
4201 tagccggcgc ttatattgcc gatatcactg atggcgatga gcgcgcgcgg cacttcggct
4261 tcatgagcgc ctgtttcggg ttcgggatgg tcgcgggacc tgtgctcggt gggctgatgg
4321 gcggtttctc cccccacgct ccgttcttcg ccgcggcagc cttgaacggc ctcaatttcc
4381 tgacgggctg tttcctttg ccggagtcgc acaaaggcga acgccggccg ttacgccggg
4441 aggctctcaa cccgctcgct tcgttccggt gggcccgggg catgaccgtc gtcgccgccc
4501 tgatggcggt cttcttcatc atgcaacttg tcggacaggt gccggccgcg ctttgggtca
4561 ttttcggcga ggatcgcttt cactgggacg cgaccacgat cggcatttcg cttgccgcat
4621 ttggcattct gcattcactc gcccaggcaa tgatcaccgg ccctgtagcc gcccggctcg
4681 gcgaaaggcg ggcactcatg ctcggaatga ttgccgacgg cacaggctac atcctgcttg
4741 ccttcgcgac acggggatgg atggcgttcc cgatcatggt cctgcttgct tcgggtggca
4801 tcggaatgcc ggcgctgcaa gcaatgttgt ccaggcaggt ggatgaggaa cgtcaggggc
4861 agctgcaagg ctcactggcg gcgctcacca gcctgacctc gatcgtcgga cccctcctct
4921 tcacggcgat ctatgcggct tctataacaa cgtggaacgg gtgggcatgg attgcaggcg
4981 ctgccctcta cttgctctgc ctgccggcgc tgcgtcgcgg gctttggagc ggcgcagggc
5041 aacgagccga tcgctgatcg tggaaacgat aggcctatgc catgcgggtc aaggcgactt
5101 ccggcaagct atacgcgccc taggagtgcg gttggaacgt tggcccagcc agatactccc
5161 gatcacgagc aggacgccga tgatttgaag cgcactcagc gtctgatcca agaacaacca
5221 tcctagcaac acgccggtcc ccgggctgag aaagcccagt aaggaaacaa ctgtaggttc
5281 gagtcgcgag atcccccgga accaaaggaa gtaggttaaa cccgctccga tcaggccgag
5341 ccacgccagg ccgagaacat tggttcctgt aggcatcggg attggcggat caaacactaa
5401 agctactgga acgagcagaa gtcctccggc cgccagttgc caggcggtaa aggtgagcag
5461 aggcacggga ggttgccact tgcgggtcag cacggttccg aacgccatgg aaaccgcccc
5521 cgccaggccc gctgcgacgc cgacaggatc tagcgctgcg tttggtgtca acaccaacag
5581 cgccacgccc gcagttccgc aaatagcccc caggaccgcc atcaatcgta tcgggctacc
5641 tagcagagcg gcagagatga acacgaccat cagcggctgc acagcgccta ccgtcgccgc
5701 gaccccgccc ggcaggcggt agaccgaaat aaacaacaag ctccagaata gcgaaatatt
5761 aagtgcgccg aggatgaaga tgcgcatcca ccagattccc gttggaatct gtcggacgat
5821 catcacgagc aataaacccg ccggcaacgc ccgcagcagc ataccggcga cccctcggcc
```

-continued

```
5881 tcgctgttcg ggctccacga aaacgccgga cagatgcgcc ttgtgagcgt ccttggggcc
5941 gtcctcctgt ttgaagaccg acagcccaat gatctcgccg tcgatgtagg cgccgaatgc
6001 cacggcatct cgcaaccgtt cagcgaacgc ctccatgggc tttttctcct cgtgctcgta
6061 aacggacccg aacatctctg gagctttctt cagggccgac aatcggatct cgcggaaatc
6121 ctgcacgtcg gccgctccaa gccgtcgaat ctgagcctta atcacaattg tcaattttaa
6181 tcctctgttt atcggcagtt cgtagagcgc gccgtgcgtc ccgagcgata ctgagcgaag
6241 caagtgcgtc gagcagtgcc cgcttgttcc tgaaatgcca gtaaagcgct ggctgctgaa
6301 cccccagccg gaactgaccc cacaaggccc tagcgtttgc aatgcaccag gtcatcattg
6361 acccaggcgt gttccaccag gccgctgcct cgcaactctt cgcaggcttc gccgacctgc
6421 tcgcgccact tcttcacgcg ggtggaatcc gatccgcaca tgaggcggaa ggtttccagc
6481 ttgagcgggt acggctcccg gtgcgagctg aaatagtcga acatccgtcg ggccgtcggc
6541 gacagcttgc ggtacttctc ccatatgaat ttcgtgtagt ggtcgccagc aaacagcacg
6601 acgatttcct cgtcgatcag gacctggcaa cgggacgttt cttgccacg gtccaggacg
6661 cggaagcggt gcagcagcga caccgattcc aggtgcccaa cgcggtcgga cgtgaagccc
6721 atcgccgtcg cctgtaggcg cgacaggcat tcctcggcct tcgtgtaata ccggccattg
6781 atcgaccagc ccaggtcctg gcaaagctcg tagaacgtga aggtgatcgg ctcgccgata
6841 ggggtgcgct tcgcgtactc caacacctgc tgccacacca gttcgtcatc gtcggcccgc
6901 agctcgacgc cggtgtaggt gatcttcacg tccttgttga cgtggaaaat gaccttgttt
6961 tgcagcgcct cgcgcgggat tttcttgttg cgcgtggtga acagggcaga gcgggccgtg
7021 tcgtttggca tcgctcgcat cgtgtccggc cacggcgcaa tatcgaacaa ggaaagctgc
7081 atttccttga tctgctgctt cgtgtgtttc agcaacgcgg cctgcttggc ctcgctgacc
7141 tgttttgcca ggtcctcgcc ggcggttttt cgcttcttgg tcgtcatagt tcctcgcgtg
7201 tcgatggtca tcgacttcgc caaacctgcc gcctcctgtt cgagacgacg cgaacgctcc
7261 acggcggccg atggcgcggg cagggcaggg ggagccagtt gcacgctgtc gcgctcgatc
7321 ttggccgtag cttgctggac catcgagccg acggactgga aggtttcgcg gggcgcacgc
7381 atgacggtgc ggcttgcgat ggtttcggca tcctcggcgg aaaaccccgc gtcgatcagt
7441 tcttgcctgt atgccttccg gtcaaacgtc cgattcattc accctccttg cgggattgcc
7501 ccgactcacg ccggggcaat gtgcccttat tcctgatttg acccgcctgg tgccttggtg
7561 tccagataat ccaccttatc ggcaatgaag tcggtcccgt agaccgtctg gccgtccttc
7621 tcgtacttgg tattccgaat cttgccctgc acgaatacca gcgaccccett gcccaaatac
7681 ttgccgtggg cctcggcctg agagccaaaa cacttgatgc ggaagaagtc ggtgcgctcc
7741 tgcttgtcgc cggcatcgtt gcgccactct tcattaaccg ctatatcgaa aattgcttgc
7801 ggcttgttag aattgccatg acgtacctcg gtgtcacggg taagattacc gataaactgg
7861 aactgattat ggctcatatc gaaagtctcc ttgagaaagg agactctagt ttagctaaac
7921 attggttccg ctgtcaagaa ctttagcggc taaaattttg cgggccgcga ccaaaggtgc
7981 gaggggcggc ttccgctgtg tacaaccaga tattttcac caacatcctt cgtctgctcg
8041 atgagcgggc catgacgaaa catgagctgt cggagagggc aggggtttca atttcgtttt
8101 tatcagactt aaccaacggt aaggccaacc cctcgttgaa ggtgatggag gccattgccg
8161 acgccctgga aactcccta cctcttctcc tggagtccac cgaccttgac cgcgaggcac
8221 tcgcggagat tgcgggtcat cctttcaaga gcagcgtgcc gcccggatac gaacgcatca
```

-continued

```
8281 gtgtggtttt gccgtcacat aaggcgttta tcgtaaagaa atggggcgac gacacccgaa
8341 aaaagctgcg tggaaggctc tgacgccaag ggtagggct tgcacttcct tctttagccg
8401 ctaaaacggc cccttctctg cgggccgtcg gctcgcgcat catatcgaca tcctcaacgg
8461 aagccgtgcc gcgaatggca tcgggcgggt gcgctttgac agttgttttc tatcagaacc
8521 cctacgtcgt gcggttcgat tagctgtttg tcttgcaggc taaacacttt cggtatatcg
8581 ttttgcctgtg cgataatgtt gctaatgatt tgttgcgtag gggttactga aaagtgagcg
8641 ggaaagaaga gtttcagacc atcaaggagc gggccaagcg caagctggaa cgcgacatgg
8701 gtgcggacct gttggccgcg ctcaacgacc cgaaaaccgt tgaagtcatg ctcaacgcgg
8761 acggcaaggt gtggcacgaa cgccttggcg agccgatgcg gtacatctgc gacatgcggc
8821 ccagccagtc gcaggcgatt atagaaacgg tggccggatt ccacggcaaa gaggtcacgc
8881 ggcattcgcc catcctggaa ggcgagttcc ccttggatgg cagccgcttt gccggccaat
8941 tgccgccggt cgtggccgcg ccaacctttg cgatccgcaa gcgcgcggtc gccatcttca
9001 cgctggaaca gtacgtcgag gcgggcatca tgacccgcga gcaatacgag gtcattaaaa
9061 gcgccgtgat tgatgatata gcggcccggc tgctcctggt tctcgcgcac cgaaatgggt
9121 gacttcacc cgcgctcttt gatcgtggca ccgatttccg cgatgctctc cggggaaaag
9181 ccggggttgt cggccgtccg cggctgatgc ggatcttcgt cgatcaggtc caggtccagc
9241 tcgataggggc cggaaccgcc ctgagacgcc gcaggagcgt ccaggaggct cgacaggtcg
9301 ccgatgctat ccaaccccag gccggacggc tgccgccgcg ctgcggcttc ctgagcggcc
9361 gcagcggtgt ttttcttggt ggtcttggct tgagccgcag tcattgggaa atctccatct
9421 tcgtgaacac gtaatcagcc agggcgcgaa cctctttcga tgccttgcgc gcggccgttt
9481 tcttgatctt ccagaccggc acaccggatg cgagggcatc ggcgatgctg ctgcgcaggc
9541 caacggtggc cggaatcatc atcttggggt acgcggccag cagctcggct tggtggcgcg
9601 cgtggcgcgg attccgcgca tcgaccttgc tgggcaccat gccaaggaat tgcagcttgg
9661 cgttcttctg gcgcacgttc gcaatggtcg tgaccatctt cttgatgccc tggatgctgt
9721 acgcctcaag ctcgatgggg gacagcacat agtcggccgc gaagagggcg gccgccaggc
9781 cgacgccaag ggtcggggcc gtgtcgatca ggcacacgtc gaagccttgg ttcgccaggg
9841 ccttgatgtt cgccccgaac agctcgcggg cgtcgtccag cgacagccgt tcggcgttcg
9901 ccagtaccgg gttggactcg atgagggcga ggcgcgcggc ctggccgtcg ccggctgcgg
9961 gtgcggtttc ggtccagccg ccggcaggga cagcgccgaa cagcttgctt gcatgcaggc
10021 cggtagcaaa gtccttgagc gtgtaggacg cattgccctg ggggtccagg tcgatcacgg
10081 caacccgcaa gccgcgctcg aaaaagtcga aggcaagatg cacaagggtc gaagtcttgc
10141 cgacgccgcc tttctggttg gccgtgacca aagttttcat cgtttggttt cctgtttttt
10201 cttggcgtcc gcttcccact tccggacgat gtacgcctga tgttccggca gaaccgccgt
10261 tacccgcgcg taccccctcgg gcaagttctt gtcctcgaac gcgcccaca cgcgatgcac
10321 cgcttgcgac actgcgcccc tggtcagtcc cagcgacgtt gcgaacgtcg cctgtggctt
10381 cccatcgact aagacgcccc gcgctatctc gatggtctgc tgccccactt ccagcccctg
10441 gatcgcctcc tggaactggc tttcggtaag ccgtttcttc atggataaca cccataattt
10501 gctccgcgcc ttggttgaac atagcggtga cagccgccag cacatgagag aagtttagct
10561 aaacatttct cgcacgtcaa caccttagc cgctaaaact cgtccttggc gtaacaaaac
10621 aaaagcccg aaaccgggct ttcgtctctt gccgcttatg gctctgcacc cggctccatc
10681 accaacaggt cgcgcacgcg cttcactcgg ttgcggatcg acactgccag cccaacaaag
```

-continued

```
10741 ccggttgccg ccgccgccag gatcgcgccg atgatgccgg ccacaccggc catcgcccac
10801 caggtcgccg ccttccggtt ccattcctgc tggtactgct tcgcaatgct ggacctcggc
10861 tcaccatagg ctgaccgctc gatggcgtat gccgcttctc cccttggcgt aaaacccagc
10921 gccgcaggcg gcattgccat gctgcccgcc gctttcccga ccacgacgcg cgcaccaggc
10981 ttgcggtcca gaccttcggc cacggcgagc tgcgcaagga cataatcagc cgccgacttg
11041 gctccacgcg cctcgatcag ctcttgcact cgcgcgaaat ccttggcctc cacggccgcc
11101 atgaatcgcg cacgcggcga aggctccgca gggccggcgt cgtgatcgcc gccgagaatg
11161 cccttcacca agttcgacga cacgaaaatc atgctgacgg ctatcaccat catgcagacg
11221 gatcgcacga acccgct
```

Plasmid pRK442(H) Sequence (SEQ. ID. 2)

```
   1 ccacccaggc cgccgccctc actgcccggc acctggtcgc tgaatgtcga tgccagcacc
  61 tgcggcacgt caatgcttcc gggcgtcgcg ctcgggctga tcgcccatcc cgttactgcc
 121 ccgatcccgg caatggcaag gactgccagc gctgccattt ttggggtgag gccgttcgcg
 181 gccgaggggc gcagccctg gggggatggg aggcccgcgt tagcgggccg ggagggttcg
 241 agaaggggg gcaccccct tcggcgtgcg cggtcacgcg cacagggcgc agccctggtt
 301 aaaaacaagg tttataaata ttggtttaaa agcaggttaa aagacaggtt agcggtggcc
 361 gaaaaacggg cggaaaccct tgcaaatgct ggattttctg cctgtggaca gccctcaaa
 421 tgtcaatagg tgcgcccctc atctgtcagc actctgcccc tcaagtgtca aggatcgcgc
 481 ccctcatctg tcagtagtcg cgcccctcaa gtgtcaatac cgcagggcac ttatccccag
 541 gcttgtccac atcatctgtg ggaaactcgc gtaaaatcag gcgttttcgc cgatttgcga
 601 ggctggccag ctccacgtcg ccggccgaaa tcgagcctgc ccctcatctg tcaacgccgc
 661 gccgggtgag tcggccctc aagtgtcaac gtccgcccct catctgtcag tgagggccaa
 721 gttttccgcg aggtatccac aacgccggcg gccgcggtgt ctcgcacacg gcttcgacgg
 781 cgtttctggc gcgtttgcag ggccatagac ggccgccagc ccagcggcga gggcaaccag
 841 cccggtgagc gtcggaaagg cgctcttccg cttcctcgct cactgactcg ctgcgctcgg
 901 tcgttcggct gcggcgagcg gtatcagctc actcaaaggc ggtaatacgg ttatccacag
 961 aatcagggga taacgcagga agaacatgt gagcaaaagg ccagcaaaag gccaggaacc
1021 gtaaaaaggc cgcgttgctg gcgtttttcc ataggctccg ccccctgac gagcatcaca
1081 aaaatcgacg ctcaagtcag aggtggcgaa acccgacagg actataaaga taccaggcgt
1141 ttccccctgg aagctccctc gtgcgctctc ctgttccgac cctgccgctt accggatacc
1201 tgtccgcctt tctcccttcg ggaagcgtgg cgccattcgc cattcaggct gcgcaactgt
1261 tgggaagggc gatcggtgcg ggcctcttcg ctattacgcc agctggcgaa aggggatgt
1321 gctgcaaggc gattaagttg ggtaacgcca gggttttccc agtcacgacg ttgtaaaacg
1381 acggccagtg aattcccggg gatccgtcga cctgcagcca agctagcttg gcgtaatcat
1441 ggtcatagct gtttcctgtg tgaaattgtt atccgctcac aattccacac aacatacgag
1501 ccggaagcat aaagtgtaaa gcctggggtg cctaatgagt gagctaactc acattaattg
1561 cgttgcgctc actgcccgct ttccagtcgg gaaacctgtc gtgccagctg cattaatgaa
1621 tcggccaacg cgcggggaga ggcggtttgc gtattgggcg ctcggtcttg ccttgctcgt
1681 cggtgatgta cttcaccagc tccgcgaagt cgctcttctt gatggagcgc atggggacgt
1741 gcttggcaat cacgcgcacc ccccggccgt tttagcggct aaaaaagtca tggctctgcc
```

-continued

```
1801 ctcgggcgga ccacgcccat catgaccttg ccaagctcgt cctgcttctc ttcgatcttc
1861 gccagcaggg cgaggatcgt ggcatcaccg aaccgcgccg tgcgcgggtc gtcggtgagc
1921 cagagtttca gcaggccgcc caggcggccc aggtcgccat tgatgcgggc cagctcgcgg
1981 acgtgctcat agtccacgac gcccgtgatt ttgtagccct ggccgacggc cagcaggtag
2041 gccgacaggc tcatgccggc cgccgccgcc ttttcctcaa tcgctcttcg ttcgtctgga
2101 aggcagtaca ccttgatagg tgggctgccc ttcctggttg gcttggtttc atcagccatc
2161 cgcttgccct catctgttac gccggcggta gccggccagc ctcgcagagc aggattcccg
2221 ttgagcaccg ccaggtgcga ataagggaca gtgaagaagg aacacccgct cgcgggtggg
2281 cctacttcac ctatcctgcc cggctgacgc cgttggatac accaaggaaa gtctacacga
2341 acccttttggc aaaatcctgt atatcgtgcg aaaaaggatg gatataccga aaaaatcgct
2401 ataatgaccc cgaagcaggg ttatgcagcg gaaaagcgcc acgcttcccg aagggagaaa
2461 ggcggacagg tatccggtaa gcggcagggt cggaacagga gagcgcacga gggagcttcc
2521 aggggggaaac gcctggtatc tttatagtcc tgtcgggttt cgccacctct gacttgagcg
2581 tcgattttttg tgatgctcgt caggggggcg gagcctatgg aaaaacgcca gcaacgcggc
2641 cttttttacgg ttcctggcct tttgctggcc ttttgctcac atgttctttc ctgcgttatc
2701 ccctgattct gtggataacc gtattaccgc ctttgagtga gctgataccg ctcgccgcag
2761 ccgaacgacc gagcgcagcg agtcagtgag cgaggaagcg gaagagcgcc agaaggccgc
2821 cagagaggcc gagcgcggcc gtgaggcttg gacgctaggg cagggcatga aaaagcccgt
2881 agcgggctgc tacgggcgtc tgacgcgtg gaaaggggga ggggatgttg tctacatggc
2941 tctgctgtag tgagtgggtt gcgctccggc agcggtcctg atcaatcgtc accctttctc
3001 ggtccttcaa cgttcctgac aacgagcctc cttttcgcca atccatcgac aatcaccgcg
3061 agtccctgct cgaacgctgc gtccggaccg gcttcgtcga aggcgtctat cgcggcccgc
3121 aacagcggcg agagcggagc ctgttcaacg gtgccgccgc gctcgccggc atcgctgtcg
3181 ccggcctgct cctcaagcac ggccccaaca gtgaagtagc tgattgtcat cagcgcattg
3241 acggcgtccc cggccgaaaa acccgcctcg cagaggaagc gaagctgcgc gtcggccgtt
3301 tccatctgcg gtgcgcccgg tcgcgtgccg gcatggatgc gcgcgccatc gcggtaggcg
3361 agcagcgcct gcctgaagct gcgggcattc ccgatcagaa atgagcgcca gtcgtcgtcg
3421 gctctcggca ccgaatgcgt atgattctcc gccagcatgg cttcggccag tgcgtcgagc
3481 agcgcccgct tgttcctgaa gtgccagtaa agcgccggct gctgaacccc caaccgttcc
3541 gccagtttgc gtgtcgtcag accgtctacg ccgacctcgt tcaacaggtc cagggcggca
3601 cggatcactg tattcggctg caactttgtc atgcttgaca ctttatcact gataaacata
3661 atatgtccac caacttatca gtgataaaga atccgcgcgt tcaatcggac cagcggaggc
3721 tggtccggag gccagacatg aaacccaaca taccctgat cgtaattctg agcactgtcg
3781 cgctcgacgc tgtcggcatc ggcctgatta tgccggtgct gccgggcctc ctgcgcgatc
3841 tggttcactc gaacgacgtc accgcccact atggcattct gctggcgctg tatgcgttgg
3901 tgcaatttgc ctgcgcacct gtgctgggcg cgctgtcgga tcgttcgggg cggcggccaa
3961 tcttgctcgt ctcgctggcc ggcgccactg tcgactacgc catcatggcg acagcgcctt
4021 tcctttgggt tctctatatc gggcggatcg tggccgcat caccggggcg actgggcgg
4081 tagccggcgc ttatattgcc gatatcactg atggcgatga gcgcgcgcgg cacttcggct
4141 tcatgagcgc ctgtttcggg ttcggatgg tcgcgggacc tgtgctcggt gggctgatgg
4201 gcggtttctc cccccacgct ccgttcttcg ccgcggcagc cttgaacggc ctcaatttcc
```

-continued

```
4261 tgacgggctg tttccttttg ccggagtcgc acaaaggcga acgccggccg ttacgccggg
4321 aggctctcaa cccgctcgct tcgttccggt gggcccgggg catgaccgtc gtcgccgccc
4381 tgatggcggt cttcttcatc atgcaacttg tcggacaggt gccggccgcg ctttgggtca
4441 ttttcggcga ggatcgcttt cactgggacg cgaccacgat cggcatttcg cttgccgcat
4501 ttggcattct gcattcactc gcccaggcaa tgatcaccgg ccctgtagcc gcccggctcg
4561 gcgaaaggcg ggcactcatg ctcggaatga ttgccgacgg cacaggctac atcctgcttg
4621 ccttcgcgac acggggatgg atggcgttcc cgatcatggt cctgcttgct cgggtggca
4681 tcggaatgcc ggcgctgcaa gcaatgttgt ccaggcaggt ggatgaggaa cgtcaggggc
4741 agctgcaagg ctcactggcg gcgctcacca gcctgacctc gatcgtcgga cccctcctct
4801 tcacggcgat ctatgcggct tctataacaa cgtggaacgg gtgggcatgg attgcaggcg
4861 ctgccctcta cttgctctgc ctgccggcgc tgcgtcgcgg gctttggagc ggcgcagggc
4921 aacgagccga tcgctgatcg tggaaacgat aggcctatgc catgcgggtc aaggcgactt
4981 ccggcaagct atacgcgccc taggagtgcg gttggaacgt tggcccagcc agatactccc
5041 gatcacgagc aggacgccga tgatttgaag cgcactcagc gtctgatcca agaacaacca
5101 tcctagcaac acggcggtcc ccgggctgag aaagcccagt aaggaaacaa ctgtaggttc
5161 gagtcgcgag atccccggga accaaaggaa gtaggttaaa cccgctccga tcaggccgag
5221 ccacgccagg ccgagaacat tggttcctgt aggcatcggg attggcggat caaacactaa
5281 agctactgga acgagcagaa gtcctccggc cgccagttgc caggcggtaa aggtgagcag
5341 aggcacggga ggttgccact tgcgggtcag cacggttccg aacgccatgg aaaccgcccc
5401 cgccaggccc gctgcgacgc cgacaggatc tagcgctgcg tttggtgtca acaccaacag
5461 cgccacgccc gcagttccgc aaatagcccc caggaccgcc atcaatcgta tcgggctacc
5521 tagcagagcg gcagagatga acacgaccat cagcggctgc acagcgccta ccgtcgccgc
5581 gaccccgccc ggcaggcggt agaccgaaat aaacaacaag ctccagaata gcgaaatatt
5641 aagtgcgccg aggatgaaga tgcgcatcca ccagattccc gttggaatct gtcggacgat
5701 catcacgagc aataaacccg ccggcaacgc ccgcagcagc ataccggcga cccctcggcc
5761 tcgctgttcg ggctccacga aaacgccgga cagatgcgcc ttgtgagcgt ccttggggcc
5821 gtcctcctgt ttgaagaccg acagcccaat gatctcgccg tcgatgtagg cgccgaatgc
5881 cacggcatct cgcaaccgtt cagcgaacgc ctccatgggc ttttctcct cgtgctcgta
5941 aacggacccg aacatctctg gagctttctt cagggccgac aatcggatct gcggaaatc
6001 ctgcacgtcg gccgctccaa gccgtcgaat ctgagcctta atcacaattg tcaattttaa
6061 tcctctgttt atcggcagtt cgtagagcgc gccgtgcgtc ccgagcgata ctgagcgaag
6121 caagtgcgtc gagcagtgcc cgcttgttcc tgaaatgcca gtaaagcgct ggctgctgaa
6181 cccccagccg gaactgaccc cacaaggccc tagcgtttgc aatgcaccag gtcatcattg
6241 acccaggcgt gttccaccag gccgctgcct cgcaactctt cgcaggcttc gccgacctgc
6301 tcgcgccact tcttcacgcg ggtggaatcc gatccgcaca tgaggcggaa ggtttccagc
6361 ttgagcgggt acggctcccg gtgcgagctg aaatagtcga acatccgtcg ggccgtcggc
6421 gacagcttgc ggtacttctc ccatatgaat ttcgtgtagt ggtcgccagc aaacagcacg
6481 acgatttcct cgtcgatcag gacctggcaa cgggacgttt tcttgccacg gtccaggacg
6541 cggaagcggt gcagcagcga caccgattcc aggtgcccaa gcggtcgga cgtgaagccc
6601 atcgccgtcg cctgtaggcg cgacaggcat tcctcggcct tcgtgtaata ccggccattg
```

-continued

```
6661 atcgaccagc ccaggtcctg gcaaagctcg tagaacgtga aggtgatcgg ctcgccgata
6721 ggggtgcgct tcgcgtactc caacacctgc tgccacacca gttcgtcatc gtcggcccgc
6781 agctcgacgc cggtgtaggt gatcttcacg tccttgttga cgtggaaaat gaccttgttt
6841 tgcagcgcct cgcgcgggat tttcttgttg cgcgtggtga acagggcaga gcgggccgtg
6901 tcgtttggca tcgctcgcat cgtgtccggc cacggcgcaa tatcgaacaa ggaaagctgc
6961 atttccttga tctgctgctt cgtgtgtttc agcaacgcgg cctgcttggc ctcgctgacc
7021 tgttttgcca ggtcctcgcc ggcggttttt cgcttcttgg tcgtcatagt tcctcgcgtg
7081 tcgatggtca tcgacttcgc caaacctgcc gcctcctgtt cgagacgacg cgaacgctcc
7141 acggcggccg atggcgcggg cagggcaggg ggagccagtt gcacgctgtc gcgctcgatc
7201 ttggccgtag cttgctggac catcgagccg acggactgga aggtttcgcg gggcgcacgc
7261 atgacggtgc ggcttgcgat ggtttcggca tcctcggcgg aaaaccccgc gtcgatcagt
7321 tcttgcctgt atgccttccg gtcaaacgtc cgattcattc accctccttg cgggattgcc
7381 ccgactcacg ccggggcaat gtgcccttat tcctgatttg acccgcctgg tgccttggtg
7441 tccagataat ccaccttatc ggcaatgaag tcggtcccgt agaccgtctg gccgtccttc
7501 tcgtacttgg tattccgaat cttgccctgc acgaatacca gcgaccccct tgcccaaatac
7561 ttgccgtggg cctcggcctg agagccaaaa cacttgatgc ggaagaagtc ggtgcgctcc
7621 tgcttgtcgc cggtcgtggc cgcgccaacc tttgcgatcc gcaagcgcgc ggtcgccatc
7681 ttcacgctgg aacagtacgt cgaggcgggc atcatgaccc gcgagcaata cgaggtcatt
7741 aaaagcgccg tgattgatga tatagcggcc cggctgctcc tggttctcgc gcaccgaaat
7801 gggtgacttc accccgcgct ctttgatcgt ggcaccgatt tccgcgatgc tctccgggga
7861 aaagccgggg ttgtcggccg tccgcggctg atgcggatct tcgtcgatca ggtccaggtc
7921 cagctcgata gggccggaac cgccctgaga cgccgcagga gcgtccagga ggctcgacag
7981 gtcgccgatg ctatccaacc ccaggccgga cggctgcgcc gcgcctgcgg cttcctgagc
8041 ggccgcagcg gtgttttttct tggtggtctt ggcttgagcc gcagtcattg ggaaatctcc
8101 atcttcgtga acacgtaatc agccagggcg cgaacctctt tcgatgcctt gcgcgcggcc
8161 gtttttcttga tcttccagac cggcacaccg gatgcgaggg catcggcgat gctgctgcgc
8221 aggccaacgg tggccggaat catcatcttg gggtacgcgg ccagcagctc ggcttggtgg
8281 cgcgcgtggc gcggattccg cgcatcgacc ttgctgggca ccatgccaag gaattgcagc
8341 ttggcgttct tctggcgcac gttcgcaatg gtcgtgacca tcttcttgat gccctggatg
8401 ctgtacgcct caagctcgat gggggacagc acatagtcgg ccgcgaagag ggcggccgcc
8461 aggccgacgc caagggtcgg ggccgtgtcg atcaggcaca cgtcgaagcc ttggttcgcc
8521 agggccttga tgttcgcccc gaacagctcg cgggcgtcgt ccagcgacag ccgttcggcg
8581 ttcgccagta ccgggttgga ctcgatgagg gcgaggcgcg cggcctggcc gtcgccggct
8641 gcgggtgcgg tttcggtcca gccgccggca gggacagcgc cgaacagctt gcttgcatgc
8701 aggccggtag caaagtcctt gagcgtgtag gacgcattgc cctgggggtc caggtcgatc
8761 acggcaaccc gcaagccgcg ctcgaaaaag tcgaaggcaa gatgcacaag ggtcgaagtc
8821 ttgccgacgc cgcctttctg gttggccgtg accaaagttt tcatcgtttg gtttcctgtt
8881 ttttcttggc gtccgcttcc cacttccgga cgatgtacgc ctgatgttcc ggcagaaccg
8941 ccgttacccg cgcgtacccc tcgggcaagt tcttgtcctc gaacgcggcc cacacgcgat
9001 gcaccgcttg cgacactgcg cccctggtca gtcccagcga cgttgcgaac gtcgcctgtg
9061 gcttcccatc gactaagacg ccccgcgcta tctcgatggt ctgctgcccc acttccagcc
```

-continued

```
9121 cctggatcgc ctcctggaac tggctttcgg taagccgttt cttcatggat aacacccata
9181 atttgctccg cgccttggtt gaacatagcg gtgacagccg ccagcacatg agagaagttt
9241 agctaaacat ttctcgcacg tcaacacctt tagccgctaa aactcgtcct tggcgtaaca
9301 aaacaaaagc ccgaaaaccg ggctttcgtc tcttgccgct tatggctctg cacccggctc
9361 catcaccaac aggtcgcgca cgcgcttcac tcggttgcgg atcgacactg ccagcccaac
9421 aaagccggtt gccgccgccg ccaggatcgc gccgatgatg ccggccacac cggccatcgc
9481 ccaccaggtc gccgccttcc ggttccattc ctgctggtac tgcttcgcaa tgctggacct
9541 cggctcacca taggctgacc gctcgatggc gtatgccgct ctccccttg gcgtaaaacc
9601 cagcgccgca ggcggcattg ccatgctgcc cgccgctttc ccgaccacga cgcgcgcacc
9661 aggcttgcgg tccagacctt cggccacggc gagctgcgca aggacataat cagccgccga
9721 cttggctcca cgcgcctcga tcagctcttg cactcgcgcg aaatccttgg cctccacggc
9781 cgccatgaat cgcgcacgcg gcgaaggctc cgcagggccg
```

The invention claimed is:

1. An in vitro method for producing proteins, the method comprising:
a.) selecting organisms which naturally produce intracytoplasmic membranes;
b.) fractioning cells of such organisms to obtain quantities of intracytoplasmic membranes;
and;
c.) combining the intracytoplasmic membranes with DNA or RNA templates that encode heterologous proteins and with a transcription/translation-competent cellular extract to create a mixture which causes simultaneous production of said heterologous proteins and their encapsulation within the intracytoplasmic membranes.

2. The method as recited in claim 1 wherein the organisms contain membrane proteins that constitute photosynthetic apparatus.

3. The method as recited in claim 2 wherein the DNA of the organism has been modified such that its intracytoplasmic membrane is devoid of light harvesting antenna and/or reaction centers of the photosynthetic apparatus.

4. An in vitro method for producing proteins, the method comprising:
a.) selecting organisms which naturally produce intracytoplasmic membranes;
b.) fractioning cells of such organisms to obtain quantities of intracytoplasmic membranes;
and;
c.) combining the intracytoplasmic membranes with DNA or RNA templates that encode the proteins and with a transcription/translation-competent cellular extract to create a mixture which causes simultaneous production of the proteins and their encapsulation within the intracytoplasmic membranes wherein the intracytoplasmic membranes are prepared from *Rhodobacter* strain modified to remove expression of photosynthetic apparati.

5. The method as recited in claim 1 wherein the protein is a membrane protein, or membrane-associated protein, or a soluble protein that interacts with a membrane-associated protein for assembly of a protein-protein complex or protein-ligand complex.

6. The method as recited in claim 1 wherein the DNA encoding the protein resides on a PCR amplicon.

7. The method as recited in claim 1 wherein the DNA encoding the protein resides on a plasmid.

8. The method as recited in claim 1 wherein the intracytoplasmic membranes embody vesicles made of membranes, or sheets made of membranes, or surfaces made of fragments of membranes.

9. An in vitro method for producing proteins, the method comprising:
a.) selecting organisms which naturally produce intracytoplasmic membranes;
b.) fractioning cells of such organisms to obtain quantities of intracytoplasmic membranes;
and;
c.) combining the intracytoplasmic membranes with DNA or RNA templates that encode the proteins and with a transcription/translation-competent cellular extract to create a mixture which causes simultaneous production of the proteins and their encapsulation within the intracytoplasmic membranes
wherein the step of mixing the intracytoplasmic membranes with the template induces transcription and translation of the template DNA.

10. An in vitro method for producing proteins, the method comprising:
a.) selecting organisms which naturally produce intracytoplasmic membranes;

b.) fractioning cells of such organisms to obtain quantities of intracytoplasmic membranes; and;
c.) combining the intracytoplasmic membranes with DNA or RNA templates that encode the proteins and with a transcription/translation-competent cellular extract to create a mixture which causes simultaneous production of the proteins and their encapsulation within the intracytoplasmic membranes
wherein RNA polymerase, derived from T7 bacteriophage, is a component of the extract.

11. An in vitro method for producing proteins, the method comprising:
a.) selecting organisms which naturally produce intracytoplasmic membranes;
b.) fractioning cells of such organisms to obtain quantities of intracytoplasmic membranes; and;
c.) combining the intracytoplasmic membranes with DNA or RNA templates that encode the proteins and with a transcription/translation-competent cellular extract to create a mixture which causes simultaneous production of the proteins and their encapsulation within the intracytoplasmic membranes
wherein unnatural amino acids, or labeled amino acids or a combination of unnatural and labeled amino acids are added to the mixture.

12. The method as recited in claim 1 wherein soluble proteins are produced and localized to aqueous phases of the mixture.

13. A method for simultaneously producing and sequestering protein, the method comprising:
a.) selecting photosynthetic organisms which naturally produce intracytoplasmic membranes;
b.) modifying DNA of the organisms such that its intracytoplasmic membrane is devoid of light harvesting antenna and/or reaction centers of the photosynthetic apparatus-to yield intracytoplasmic membranes with reduced content;
c.) culturing the modified organism to express modified intracytoplasmic membranes; and
d.) mixing the modified intracytoplasmic membranes with DNA templates or RNA templates that encode heterologous protein so as to cause simultaneous production of said heterologous protein and encapsulation of said heterologous protein within the intracytoplasmic membranes.

14. The method as recited in claim 13 wherein the mixing step further comprises a transcription/translation-competent cellular extract mixed with the modified intracytoplasmic membranes and the DNA templates or RNA templates.

15. The method as recited in claim 13 wherein the organisms contain membrane proteins that constitute photosynthetic apparatus.

16. The method as recited in claim 13 wherein the organisms are *Rhodobacter* bacteria.

17. The method as recited in claim 13 wherein the protein is a membrane protein, or membrane-associated protein, or a soluble protein that interacts with a membrane-associated protein for assembly of a protein-protein complex or protein-ligand complex.

18. The method as recited in claim 13 wherein the DNA encoding the protein resides on a PCR amplicon.

19. The method as recited in claim 13 wherein the DNA encoding the protein resides on a plasmid.

20. The method as recited in claim 13 wherein the intracytoplasmic membranes define vesicles made of membranes, or sheets made of membranes, or other surfaces made of membranes and fragments of membranes.

* * * * *